United States Patent [19]

Minagawa et al.

[11] Patent Number: 4,477,616
[45] Date of Patent: Oct. 16, 1984

[54] TETRA-(2,2,6,6-TETRAMETHYL-4-PIPERIDINYL)-3-METHYL-5-(1'2'-BISCARBOXYLATE)-ETHYL-CYCLOHEXANE OR 3-CYCLOHEXENE-1,2-DICARBOXYLATES AND SYNTHETIC RESIN COMPOSITIONS CONTAINING THE SAME

[75] Inventors: Motonobu Minagawa, Koshigaya; Yutaka Nakahara, Iwatsuki; Toshihiro Shibata, Omiya, all of Japan

[73] Assignee: Adeka Argus Chemical Co., Ltd., Urawa, Japan

[21] Appl. No.: 471,913

[22] Filed: Mar. 3, 1983

[30] Foreign Application Priority Data

Mar. 9, 1982 [JP] Japan .................................. 57-36796

[51] Int. Cl.³ ........................ C08K 5/34; C07D 401/00
[52] U.S. Cl. .................................... 524/102; 546/187; 546/188; 546/190; 546/191
[58] Field of Search ................... 524/102, 112; 528/93; 546/186, 187, 188, 190, 191

[56] References Cited

U.S. PATENT DOCUMENTS 4,101,508  7/1978  Minagawa et al. .................. 524/99
4,210,577  7/1980  Minagawa et al. .................. 524/102
4,271,079  6/1981  Maeda et al. ........................ 528/93

Primary Examiner—John Kight
Assistant Examiner—Kriellion Morgan

[57] ABSTRACT

Tetra-2,2,6,6-tetramethyl-4-piperidinyl)-3-methyl-5-(1',2'-biscarboxylate)-ethyl-cyclohexane or 3-cyclohexene-1,2-dicarboxylates are provided having the formula (I) or (II):

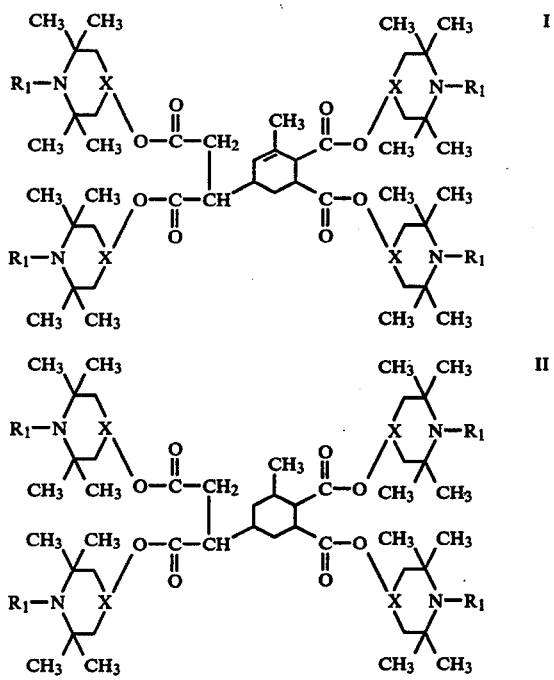

wherein:
$R_1$ is selected from the group consisting of hydrogen, —O, alkyl, hydroxy alkyl and epoxyalkyl having from one to about eighteen carbon atoms, acyl having from one to about eighteen carbon atoms, cycloalkyl having from three to about eighteen carbon atoms; phenyl; phenalkyl and alkylphenyl having from seven to about twenty-four carbon atoms;
$R_2$ is lower alkyl having from one to about six carbon atoms; and
X is selected from the group consisting of:

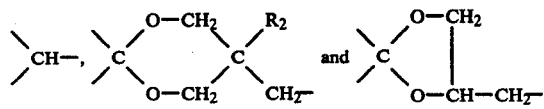

as well as stabilized synthetic resin compositions comprising such piperidinyl compounds.

36 Claims, No Drawings

TETRA-(2,2,6,6-TETRAMETHYL-4-PIPERIDINYL)-3-METHYL-5-(1'2'-BISCARBOXYLATE)-ETHYL-CYCLOHEXANE OR 3-CYCLOHEXENE-1,2-DICARBOXYLATES AND SYNTHETIC RESIN COMPOSITIONS CONTAINING THE SAME

Polymers such as polyethylene, polypropylene, ABS resin, polyvinyl chloride and polyurethane undergo degradation and discoloration when subjected to irradiation by ultraviolet light such as sunlight, with deterioration in mechanical strength. Accordingly, various kinds of light stabilizers have been incorporated in such polymers to lessen their deterioration. However, the available stabilizers are unsatisfactory in their stabilizing effectiveness, unstable to heat and oxidation, and soluble in water or organic solvents. Some stabilizers even impart a color of their own to the polymers.

2,2,6,6-tetramethyl piperidine compounds do not impart color to the polymer, and act as quenchers. Many piperidine compounds, therefore, are proposed as light stabilizers.

Minagawa et al U.S. Pat. No. 4,101,508, patented July 18, 1978, proposes 2,2,6,6-tetramethyl-4-piperidyl esters of bicyclic heptane and octane carboxylic acids, useful as stabilizers for organic polymeric materials, and having the general formula:

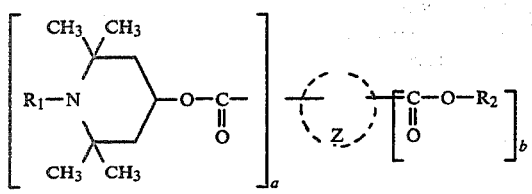

$R_1$ is selected from the group consisting of hydrogen and O;

$R_2$ is selected from the group consisting of alkyl; alkenyl; cycloalkyl; aryl; alkaryl; aralkyl;

a is selected from the group consisting of 1, 2, 3 and 4;

b is selected from the group consisting of 0, 1, 2 and 3; and a+b is 1, 2, 3 or 4; and Z is a bicyclic heptane or octane ring having from seven to eight ring carbon atoms.

When b=0, the compounds take the form:

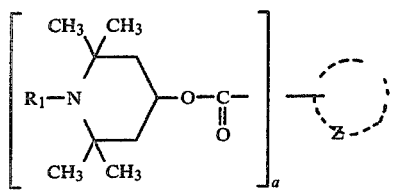

where the $R_1$, a and Z are as defined in formula I.

When b=1, the compounds take the form:

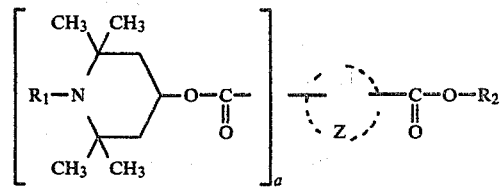

Hindered 2,2,6,6-tetraalkyl-4-carboxylic acid ester piperidine compounds have been proposed by Murayama et al U.S. Pat. No. 3,640,928 patented Feb. 8, 1972 as light and heat stabilizers for synthetic polymers, such as polyolefins, polyvinyl chloride, polyvinylidene chloride, polyurethanes, and polyamides. These compounds have the general formula:

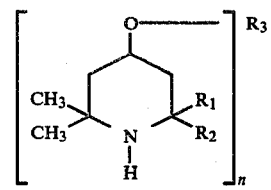

or a salt thereof.

In the above formula:

$R_1$ and $R_2$, which may be the same or different, each are an alkyl group such as methyl, ethyl, isopropyl or dodecyl, or they form, together with the carbon atom to which they are attached, a saturated alicyclic group such as:

or a group of the formula

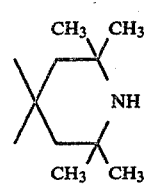

n is an integer of 1 to 3 inclusive; and $R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

The bicarbocyclic heptane and octane rings can carry from one to four substituents selected from the group consisting of halogen (chlorine, bromine, fluorine or iodine), alkyl, cycloalkyl and aryl.

Minagawa et al U.S. Pat. No. 4,136,081, patented Jan. 23, 1979, provides 2,2,6,6-tetramethyl-4-piperidyl carboxylic acid esters of aliphatic tetracarboxylic acids, useful as stabilizers for organic polymeric materials, and having the general formula:

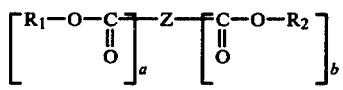

wherein:

$R_1$ is selected from the group consisting of

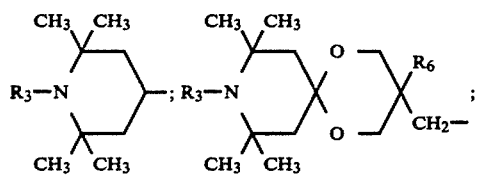

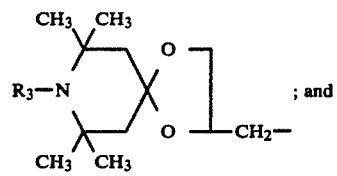

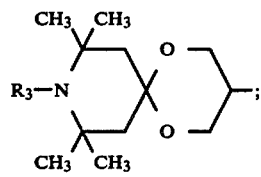

and when a is 2, 3 or 4, the $R_1$ groups can be the same or different;

$R_2$ is selected from the group consisting of hydrogen; alkyl; alkenyl; cycloalkyl; alkcycloalkyl; cycloalkalkyl; aryl; aralkyl; and alkaryl; and when b is 2 or 3, the $R_2$ groups can be the same or different;

$R_3$ is selected from the group consisting of hydrogen and O;

$R_6$ is lower alkyl;

a is selected from the group consisting of 1, 2, 3 and 4;

b is selected from the group consisting of 0, 1, 2 and 3;

a+b is equal to 4; and Z is a tetravalent aliphatic or cycloaliphatic radical carrying four

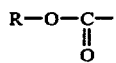

groups, where R is $R_1$ or $R_2$, and can include from one to three hydroxyl groups OH.

Murayama et al U.S. Pat. No. 4,212,974, patented July 15, 1980, provides piperidine derivatives having the formula:

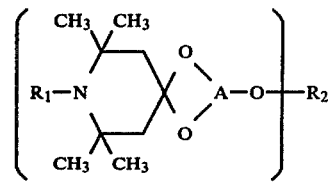

wherein $R_1$ represents hydrogen, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4; when n is 1, $R_2$ represents hydrogen atom, an aliphatic, aromatic or heterocyclic monacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group

in which $R_3$ represents hydrogen atom, a lower alkyl group or phenyl group and $R_4$ represents an alkyl group; when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid; when n is 3, $R_2$ represents an aromatic triacyl group or a trivalent group from an oxoacid; and when n is 4, $R_2$ represents an aromatic tetraacyl group, and A represents a group

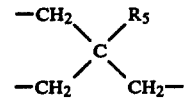

in which $R_5$ represents hydrogen atom or a lower alkyl group or, when n is 1, $R_5$ may represent together with $R_2$ a group

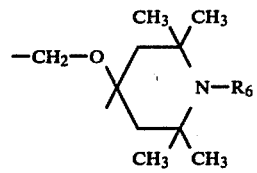

in which $R_6$ represents the same group as defined in $R_1$ and may be the same or different from $R_1$, or a group

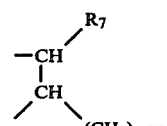

in which n is 1 or 2 and $R_7$ represents hydrogen atom or, when n and m are 1, $R_7$ represents methylene group together with $R_2$.

These piperidine derivatives have a stabilizing effect against photo- and thermal-deterioration of synthetic polymeric materials such as polyolefin; polyvinyl chloride, polyvinylidene chloride, polyacetal, polyester, polyamide, polyurethane, epoxy resins and the like.

The known piperidine compounds are also unsatisfactory in their stabilizing effectiveness, are volatile and lost from the polymer at high temperatures and are extracted by water.

In accordance with the present invention, tetra-(2,2,6,6-tetramethyl-4-piperidinyl)-3-methyl-5-(1',2'-bis-carboxylate)ethyl-cyclohexane or 3-cyclohexene-1,2-dicarboxylates are provided having the formula (I) or (II):

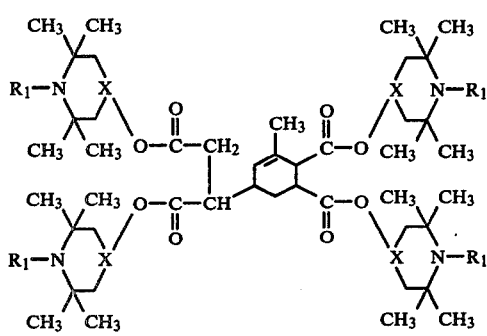

I

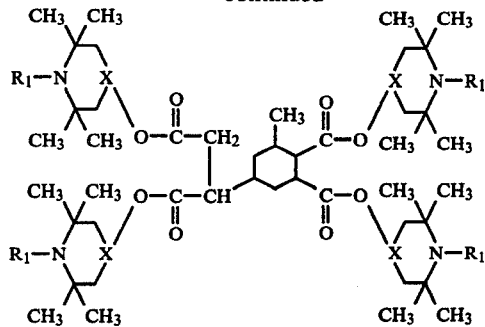

II wherein:

$R_1$ is selected from the group consisting of hydrogen, —O, alkyl, hydroxy alkyl and epoxyalkyl having from one to about eighteen carbon atoms, acyl having from one to about eighteen carbon atoms, cycloalkyl having from three to about eighteen carbon atoms; phenyl; phenalkyl and alkylphenyl having from seven to about twenty-four carbon atoms;

$R_2$ is lower alkyl having from one to about six carbon atoms; and

X is selected from the group consisting of:

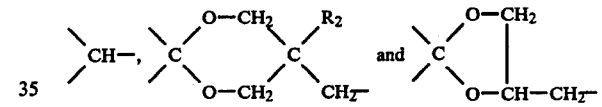

as well as stabilized synthetic resin compositions comprising such piperidinyl compounds.

The piperidinyl carboxylic acid esters of the invention accordingly include the following six subgenera:

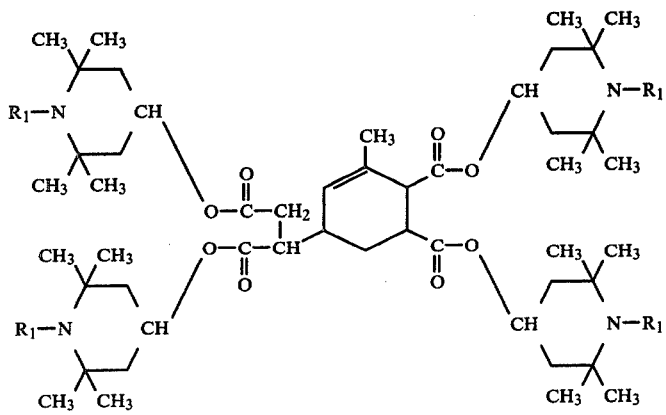

III

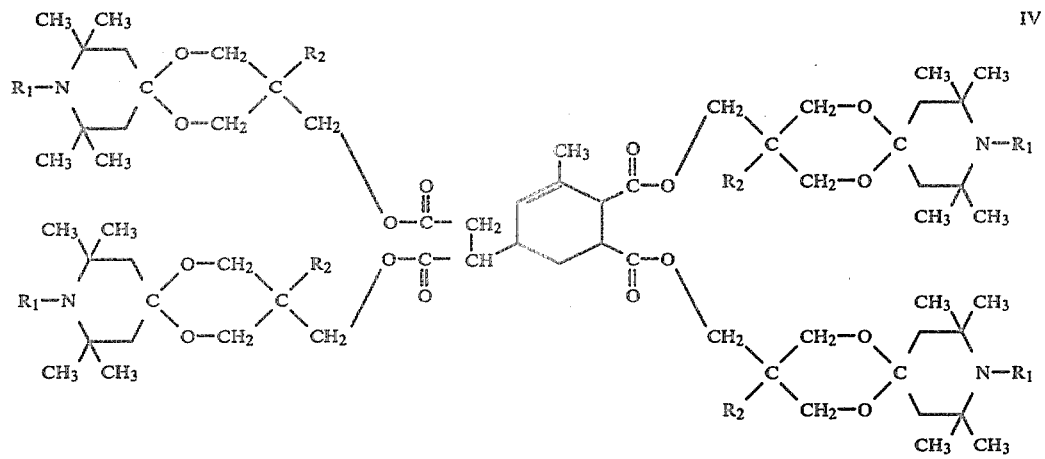
IV
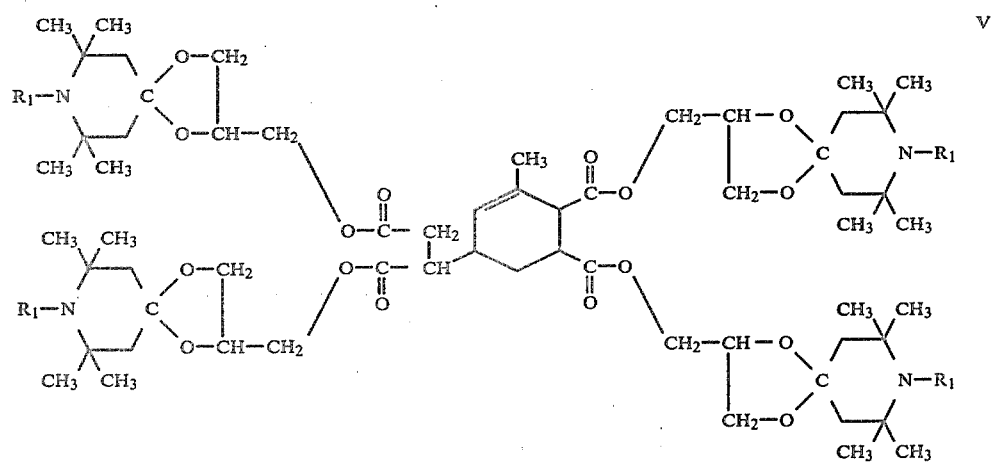
V
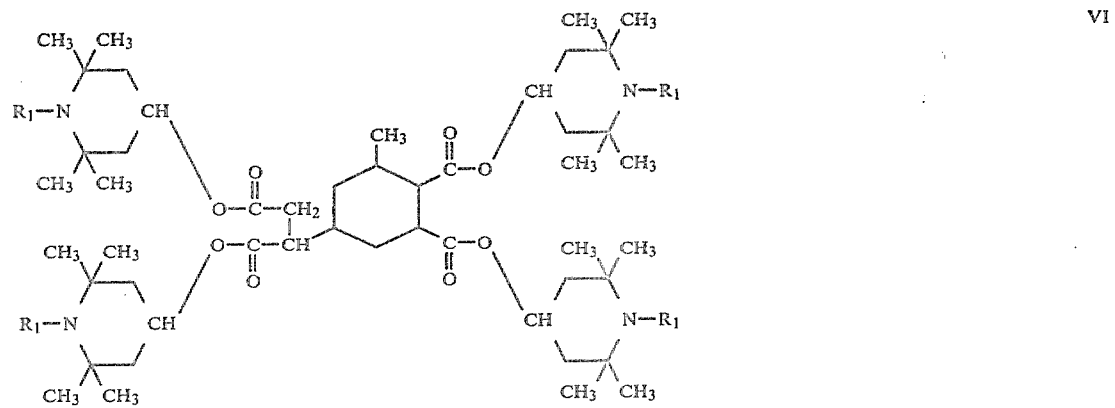
VI

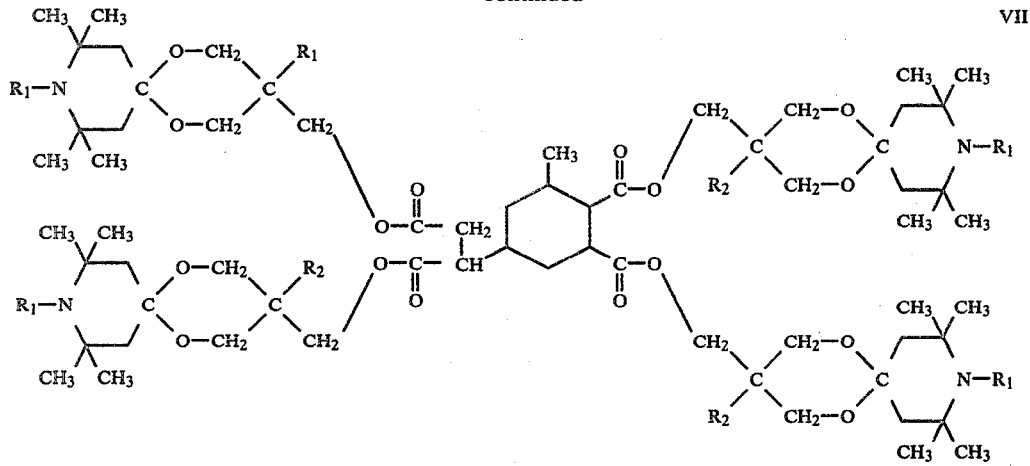

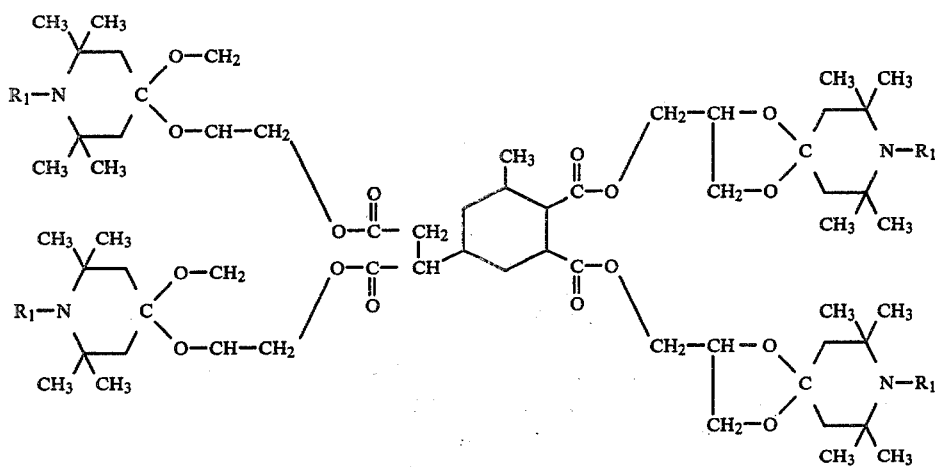

Exemplary $R_1$ alkyl are methyl, ethyl, propyl, isopropyl, butyl, isobutyl, tert-butyl, sec-butyl, amyl, isoamyl, tert amyl, hexyl, heptyl, octyl, isooctyl, 2-ethylhexyl, nonyl, isononyl, decyl, undecyl, dodecyl, palmityl, myristyl, stearyl, cyclopropyl, cyclobutyl, cyclopentyl, cyclohexyl, cycloheptyl, cyclooctyl, benzyl, phenethyl, phenbutyl, phenhexyl, tolyl, xylyl, mesityl, butylphenyl, octylphenyl, nonylphenyl, dodecylphenyl, 2-hydroxyethyl, 2-hydroxypropyl, 2-hydroxybutyl, 2,3-epoxypropyl, 2,3-epoxybutyl, 1,2-epoxy butyl, 1,2-epoxyamyl.

Exemplary $R_1$ acyl are acetyl, propionyl, butyroyl, octanoyl, lauroyl, stearoyl, palmitoyl and myristoyl.

Exemplary $R_2$ lower alkyl are methyl, ethyl, propyl, isopropyl, butyl, isobutyl, tert-butyl, isoamyl, amyl, hexyl and isohexyl.

Typical examples of piperidinyl compounds of above formulae (I) to (VIII) are:

1.

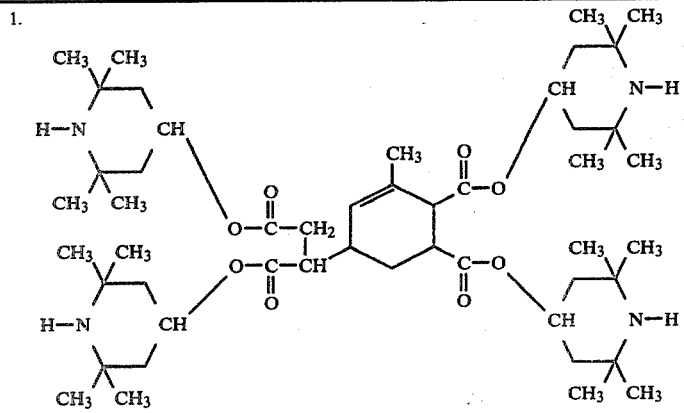

2. 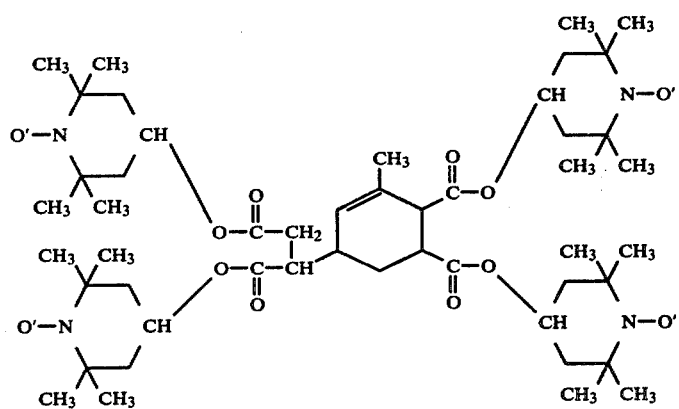
3. 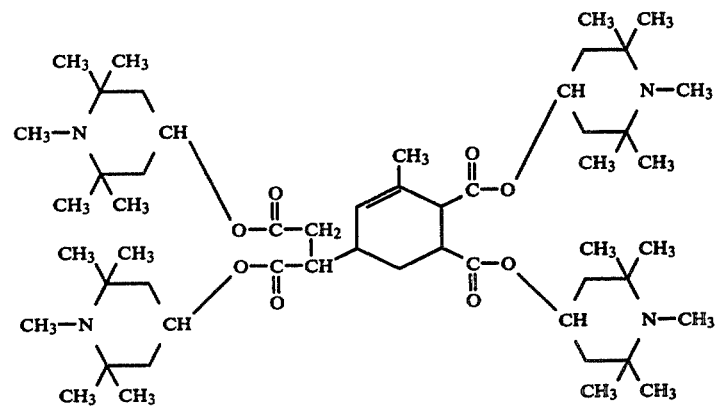
4. 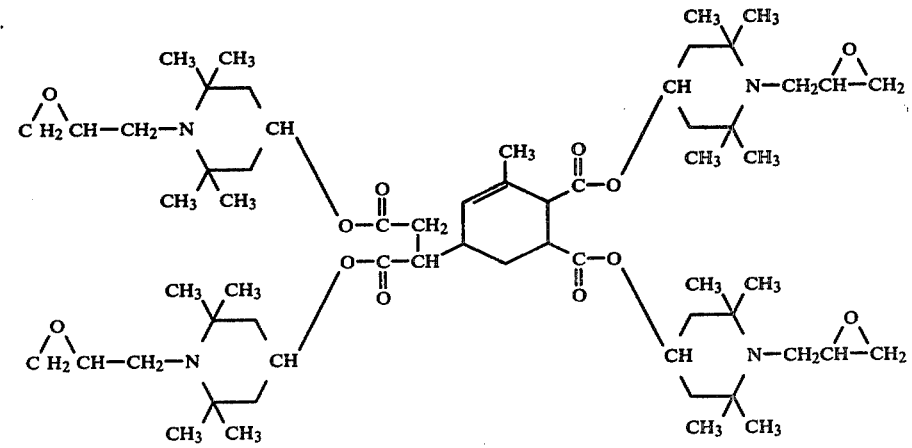

-continued
5.
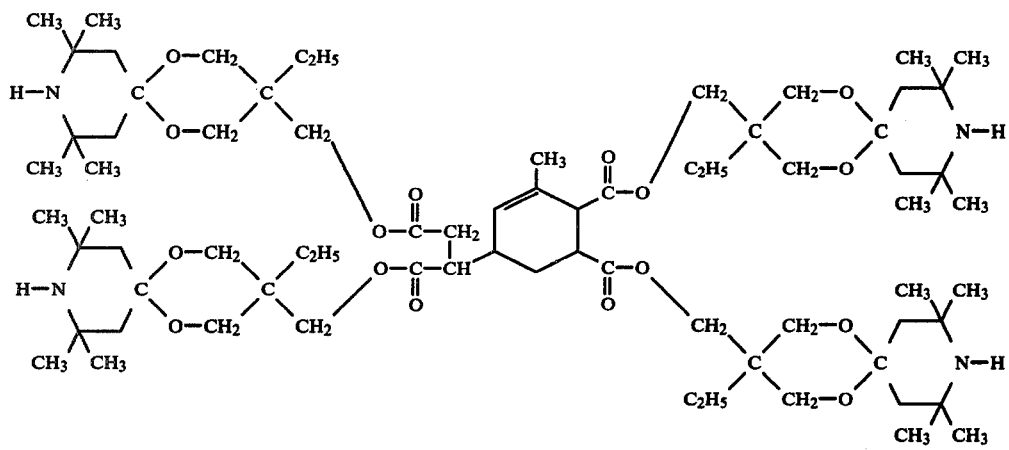
6.
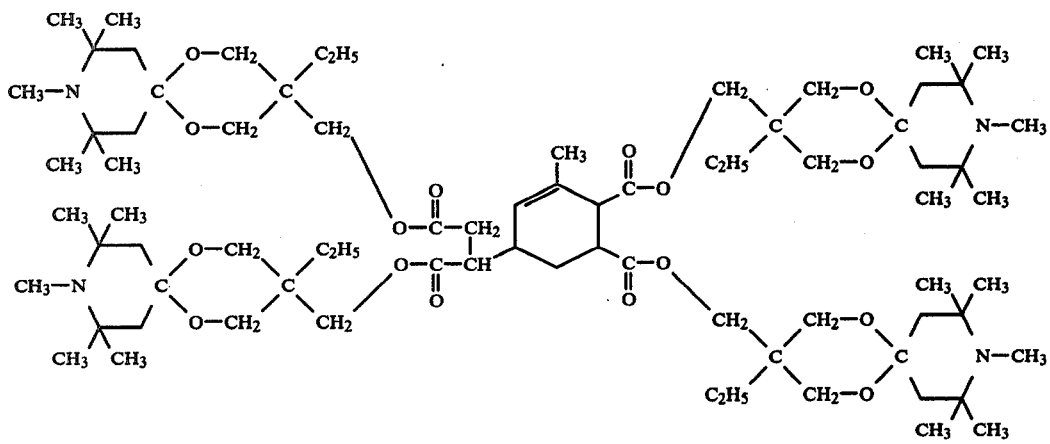
7.
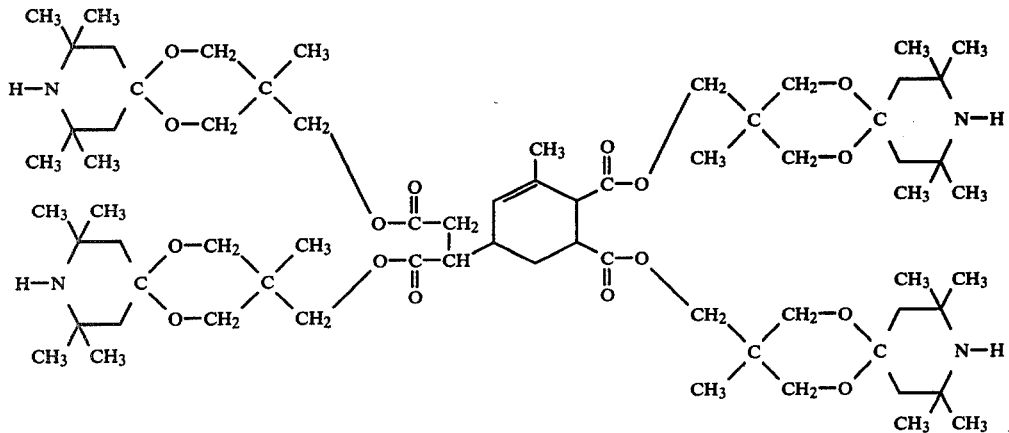

-continued
8. 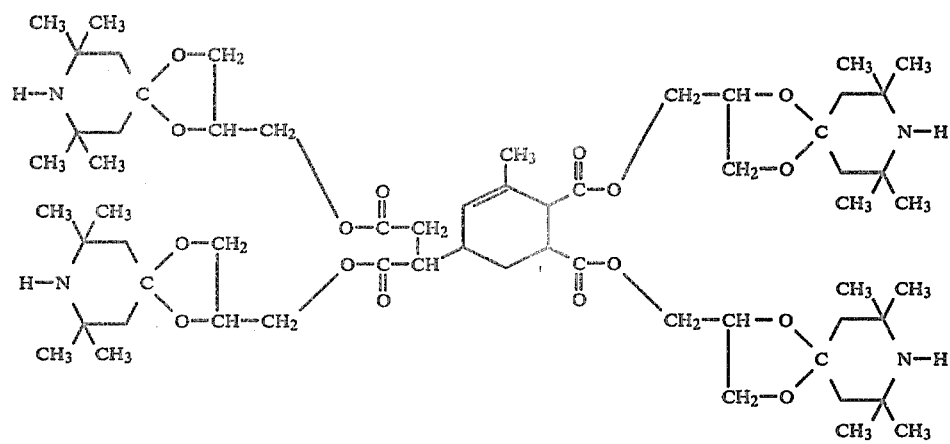
9. 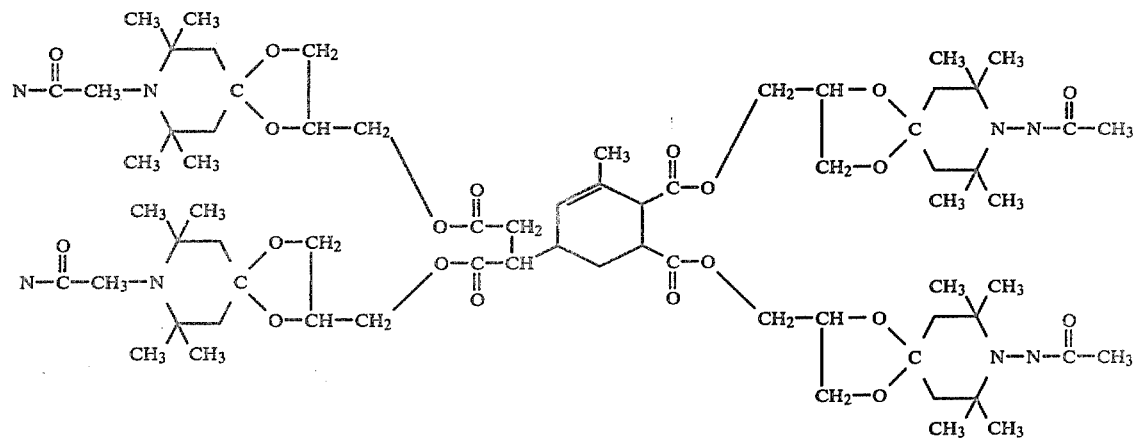
10. 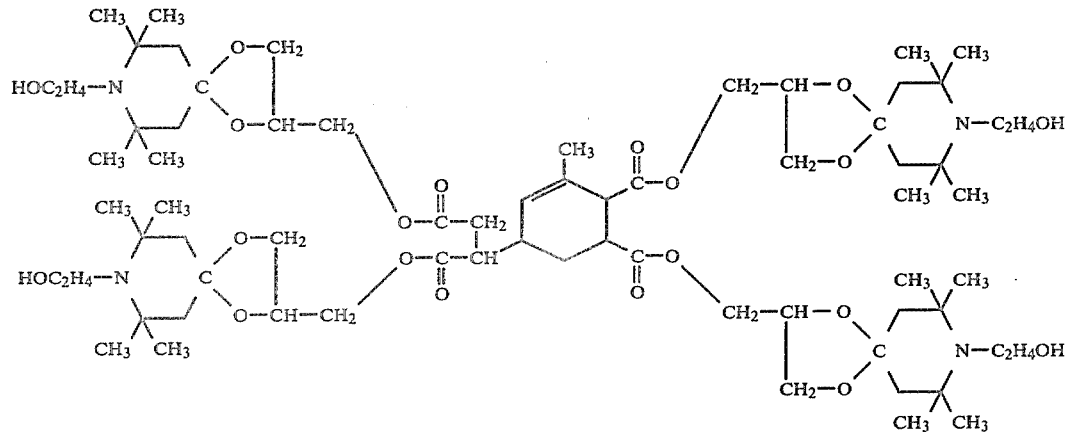

11. 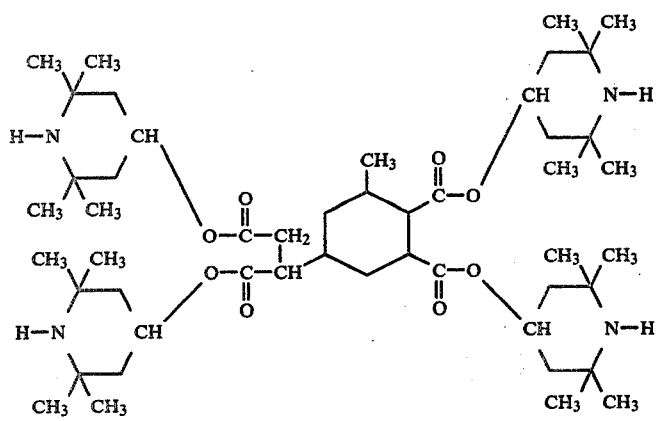
12. 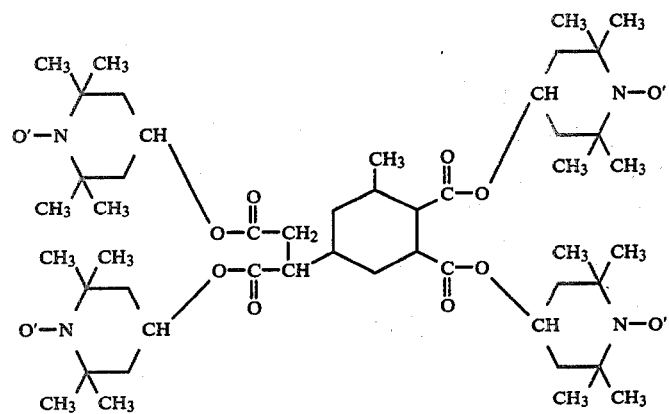
13. 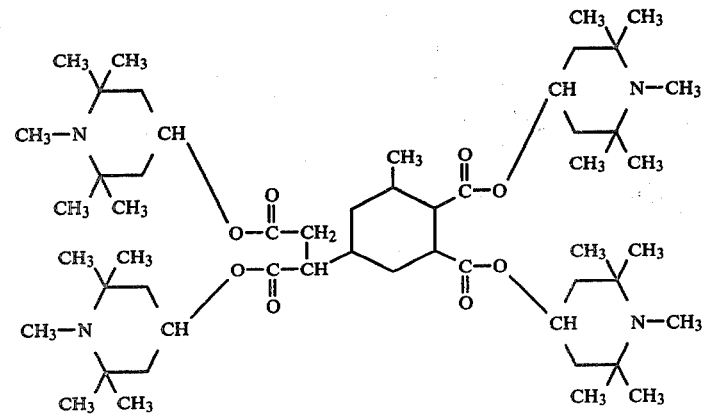

-continued
14. 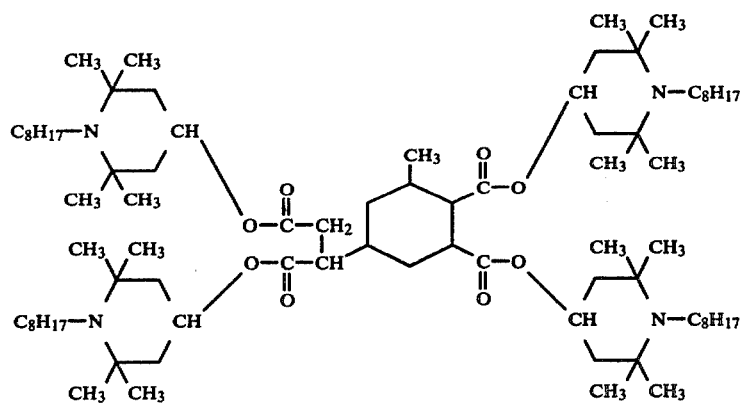
15. 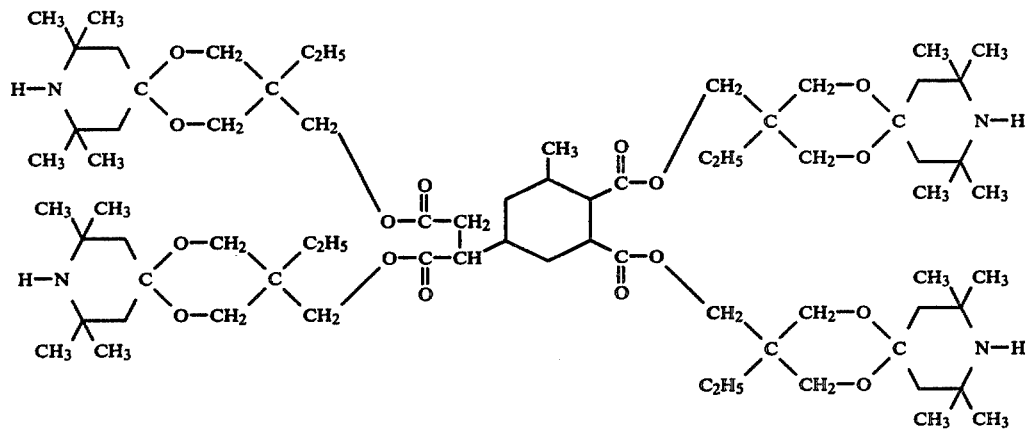
16. 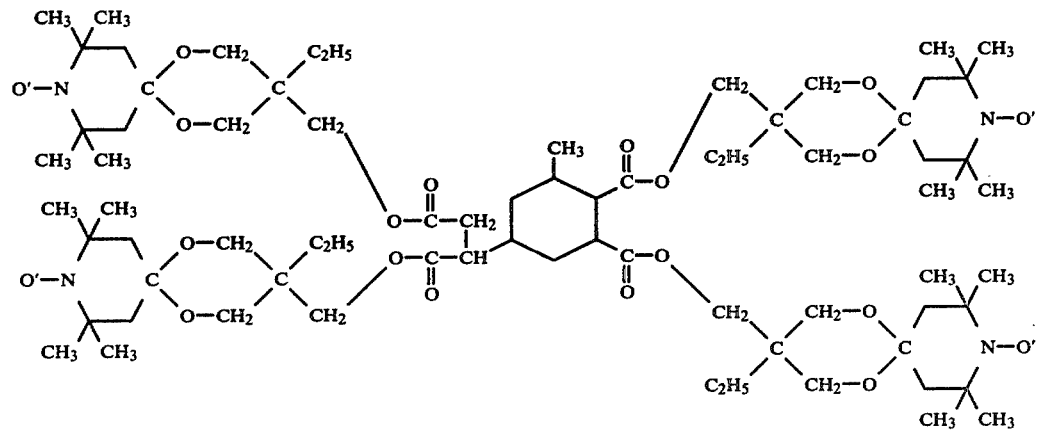
17.

-continued
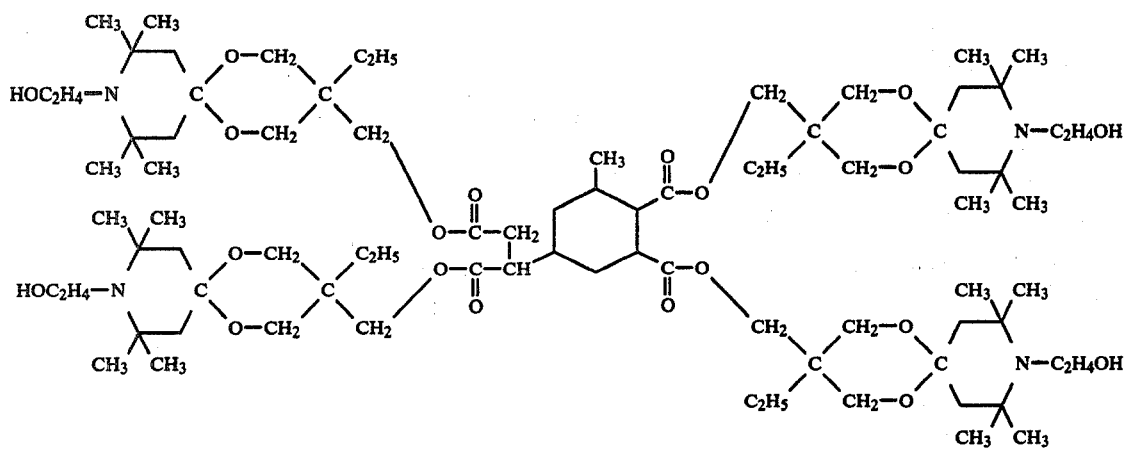
18. 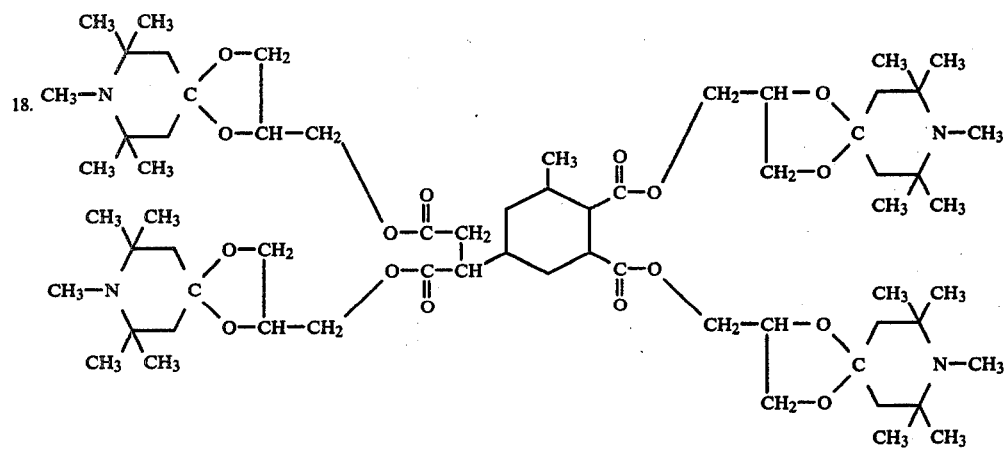
19. 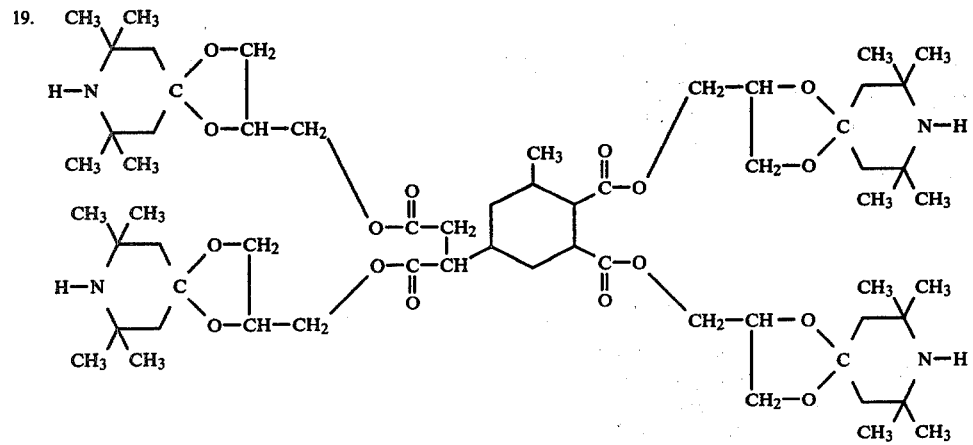

-continued

20. 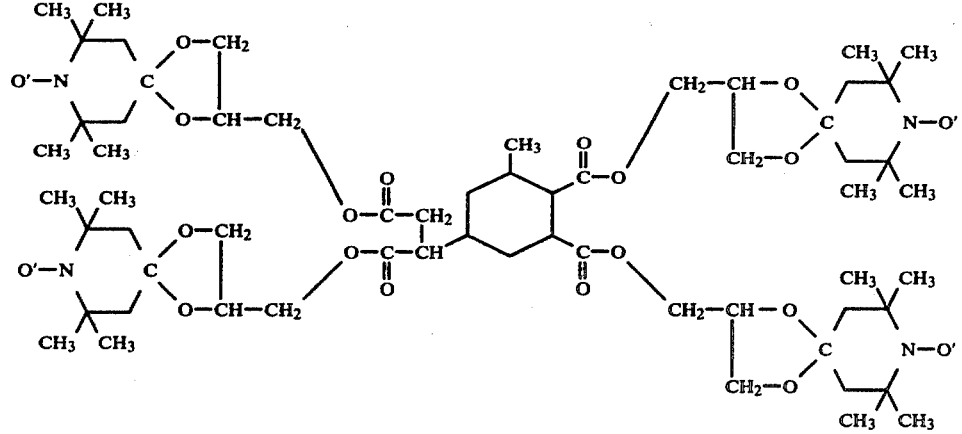

21. 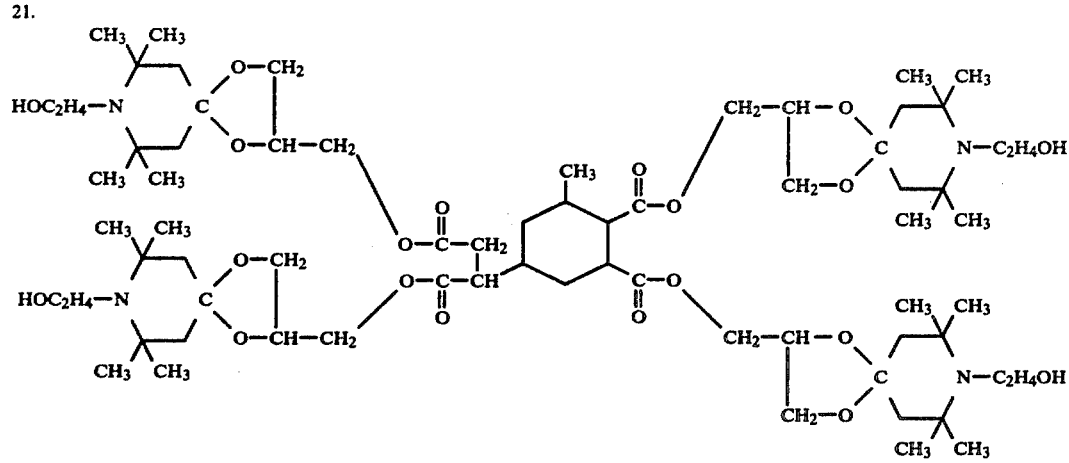

22. 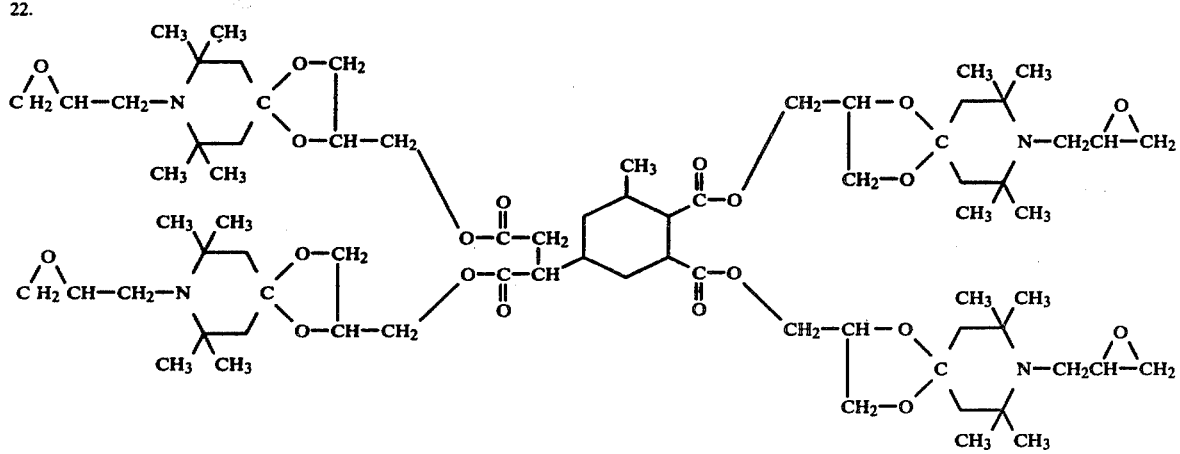

The compounds of formulae I and II can be easily prepared by the reaction of the corresponding piperidinyl alcohol with the corresponding cyclohexane or 3-cyclohexene carboxylic acid ester, anhydride or acid chloride. Such carboxylic acids are disclosed in Japan Kokai No. 80-36406, and are obtained by the reaction of piperylene with maleic anhydride.

EXAMPLE I

Synthesis of

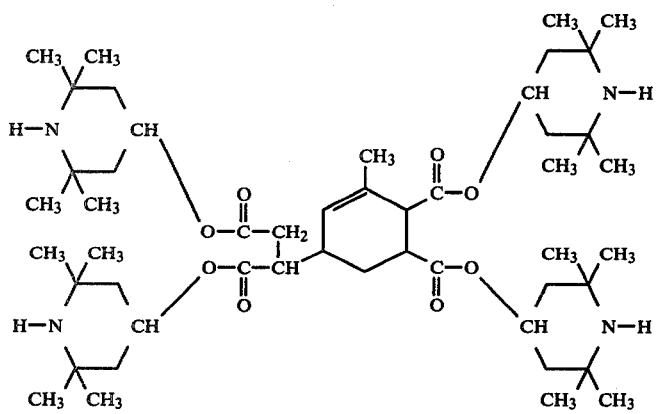

2,2,6,6-Tetramethyl-4-piperidinol 13.2 g, dimethyl-5-(1',2'-biscarbomethoxy) ethyl-3-methyl-3-cyclohexene-1,2-dicarboxylate 7.1 g, xylene 50 ml and tetraisopropyltitanate 1.5 ml were stirred at 130° to 140° C. for 8 hours under a stream of nitrogen. Then the mixture was cooled, and 50 ml of xylene was added, and the solution washed and dried. The xylene was removed by evaporation, and the residue was recrystallized from n-hexane. The product was obtained as white powder.

Elemental analysis:

|  | C % | H % | N % |
|---|---|---|---|
| Found. | 68.83 | 9.85 | 6.43 |
| Calcd. | 68.69 | 9.81 | 6.54 |

The compound accordingly corresponded to the above structure.

Small amounts of the tetrapiperidinyl esters of this invention when combined with synthetic resin improve the light stability of the resin. The amount of the tetrapiperidinyl esters is generally within the range from about 0.001 to about 5 parts by weight, preferably from about 0.01 to about 3 parts by weight, per 100 parts by weight of resin.

Synthetic resins that can have their resistance to deterioration enhanced with tetrapiperidinyl esters according to this invention include α-olefin polymers such as polyethylene, polypropylene, polybutene, poly-3-methylbutene, or mixtures thereof, and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The tetrapiperidinyl esters of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thioether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including an alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

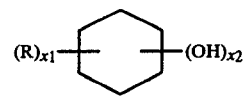

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

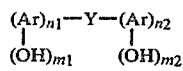

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl, or cycloalkyl, or thiohydrocarbon groups having from one to about thirty carbon atoms, and carboxyl

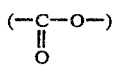

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

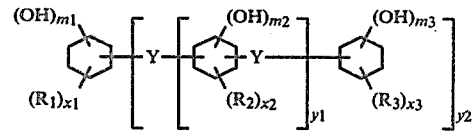

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

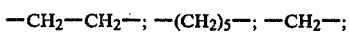

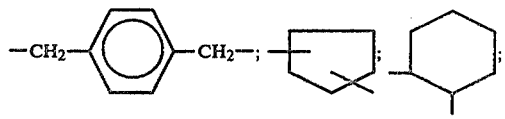

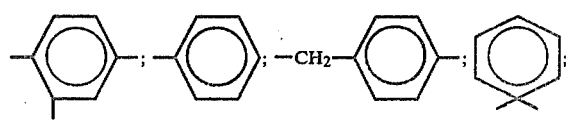

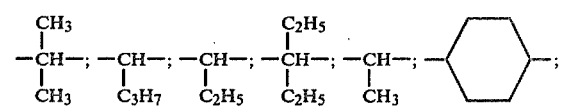

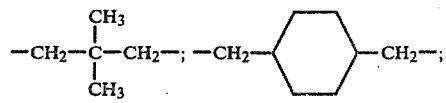

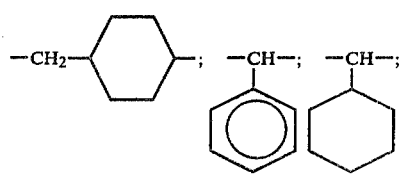

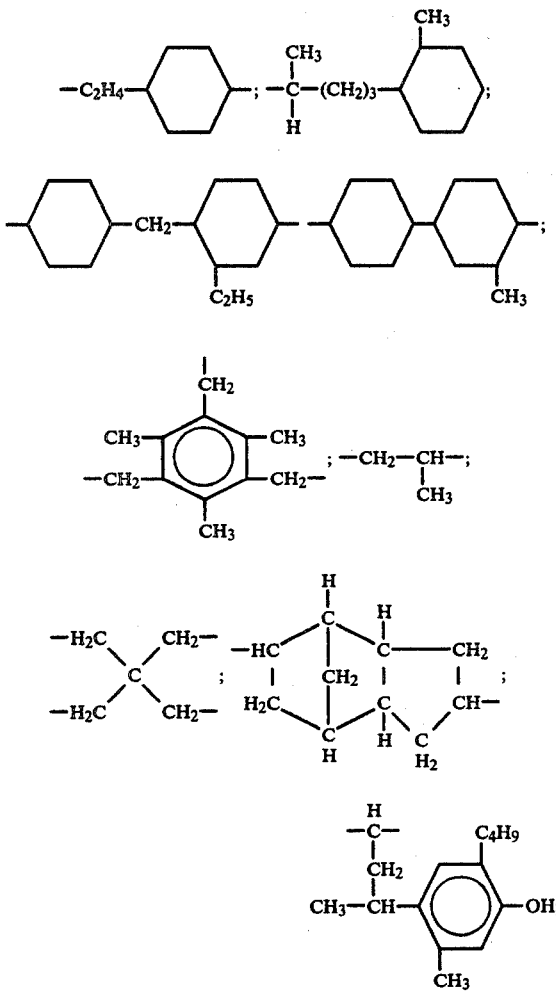

(2) Y groups where only atoms other than carbon link the aromatic rings, such as

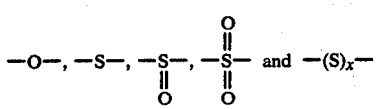

where x is a number from one to ten;

(3) Y groups made up to more than a single atom including both carbon and other atoms linking the aromatic nuclei, such as:

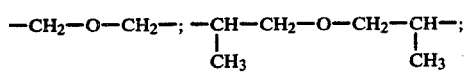

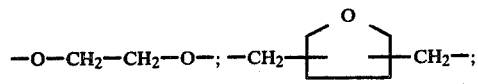

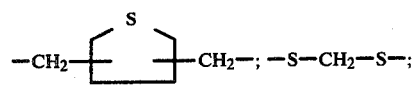

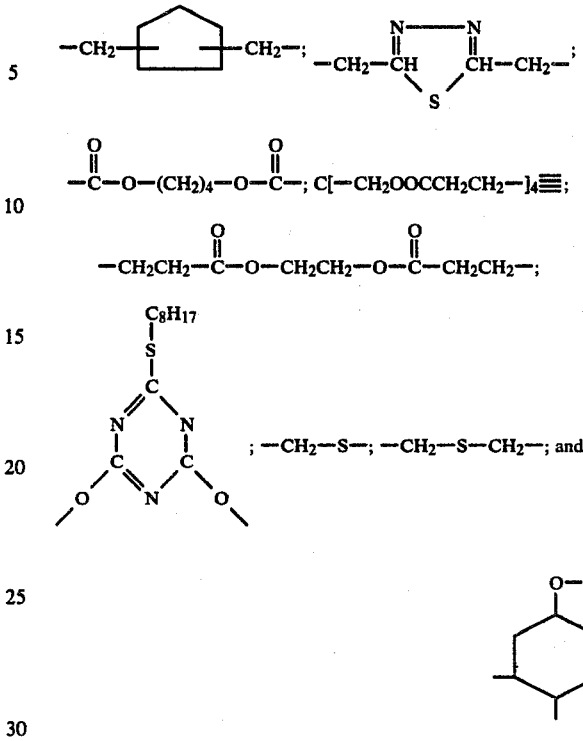

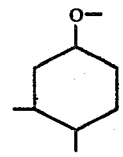

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxyphenol, p-n-decyloxy-cresol, nonyl-n-decyloxycresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-di-chlorobenzoyl-aminophenol, p-hydroxysalicyl anilide, stearyl-(3,5-di-methyl-4-hydroxy-benzyl) thioglycolate, stearyl-β-(4-hydroxy-3,5-di-t-butylphenyl) propionate, distearyl-3,5-di-t-butyl-4-hydroxybenzylphosphonate, and distearyl (4-hydroxy-3-methyl-5-t-butyl) benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis-(2-tertiary-butyl-5-methyl-phenol), 4,4'-cyclo-hexylidene bis-(2-tertiary-butylphenol), 2,2'- methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl) butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methylphenol), 2,2'-methylene-bis-(4-methyl-6-(1'-methyl-cyclohexyl)phenol, 4,4'-cyclohexylene bis-(2-tertiary-butyl-phenol), 2,6-bis-(2'-hydroxy-3'-t-butyl-5'-methyl-benzyl)-4-methyl-phenol, hydroxy-3-t-butylphenyl) butyric acid] glycol ester, 4,4'-butylidene-bis-(6-t-butyl-m-cresol), 1,3,3-tris-(2-methyl-4-hydroxy-5-t-butylphenol) butane, 1,3,5-tris-(3,5-di-t-butyl-4-hydroxybenzyl)-2,4,6-trimethylbenzene, tetrakis [methylene-3 (3,5-di-t-butyl-4-hydroxyphenyl)propionate] methane, 1,3,5-tris-(3,5-di-t-butyl-4-hydroxybenzyl) isocyanurate, 1,3,5-tris-(3,5-di-t-butyl-4-hydroxyphenyl) propionyl-oxyethyl isocyanurate, 2-octylthio-4,6-di-(4-hydroxy-3,5-di-t-butyl) phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

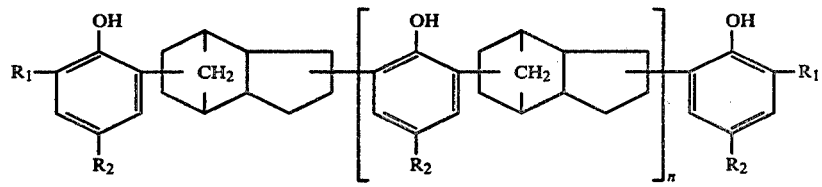

4,4'-oxobis (naphthalene-1,5-diol), 1,3'-bis-(naphthalene-2,5-diol) propane, and 2,2'-butylene bis-(naphthalene-2,7-diol), (3-methyl-5-tert-butyl-4-hydroxyphenol)-4'-hydroxy-phenyl) propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl) ethane, (2-hydroxyphenyl)-(3',5'-di-tert-butyl-4',4-hydroxyphenyl) ethane, in which
R$_1$ and R$_2$ are lower alkyl, and can be the same or different, and
n is the number of the groups enclosed by the brackets and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

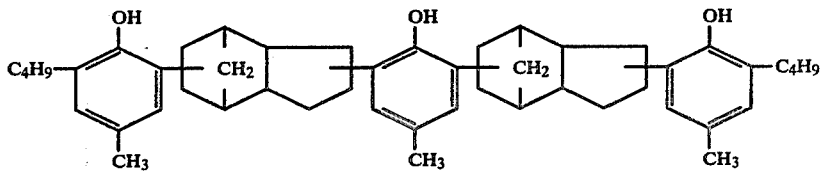

2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl) thiazolo-(5,4-d) thiazole, 2,2'-bis-(3-methyl-5-t-butyl-4-hydroxyphenyl) thiazole-(5,4-d)-thiazole, 4,4'-bis-(4-hydroxyphenyl) pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl) sulfide, bis-(2-tert-butyl-4-hydroxy-5-methylphenyl) sulfide, bis-(2-tert-butyl-4-hydroxy-5-methylphenyl)sulfoxide, bis-(3-ethyl-5-tert-butyl-4-hydroxybenzyl) sulfide, bis-(2-hydroxy-4-methyl-6-tert-butyl-phenyl) sulfide, 4,4'-bis-(4-hydroxyphenol) pentanoic acid octadecyl thiopropionate ester, 1,1,3-tris-(2'-methyl-4-hydroxy-5'-tert-butylphenyl) butane, 1,1,3-tris-(1-methyl-3-hydroxy-4-tert-butylphenyl) butane, 1,8-bis-(2-hydroxy-5-methyl-benzoyl-n-octane, 2,2'-ethylene-bis-[4'-(3-tert-butyl-4-hydroxyphenyl)-thiazole],1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the tetrapiperidinyl esters is used with a polyvalent metal salt or an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

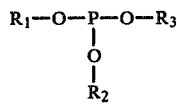

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

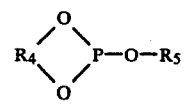

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$, $R_5$ is hydrogen or a cation, in the case of the acid phosphites.

Also useful organic triphosphites are mixed heterocyclic-open chain phosphites of the type:

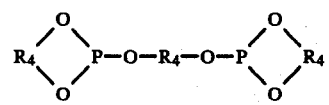

More complex triphosphites are formed from trivalent organic radicals, of the type:

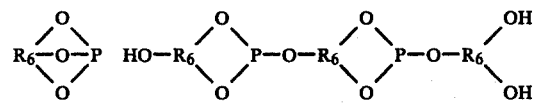

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

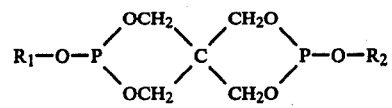

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxy groups on either or both of the aromatic rings. These phosphites are characterized by the formula:

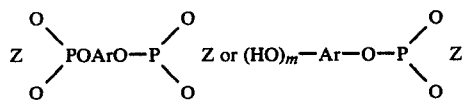

in which

Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, dephenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl) phosphite, trioctadecyl phosphite, triisooctyl phosphite, tridodecyl phosphite, isooctyl diphenyl phosphite, diisooctyl phenyl phosphite, tri(t-octylphenyl) phosphite, tri-(t-nonylphenyl) phosphite, benzyl methyl isopropyl phosphite, butyl dicresyl phosphite, isooctyl di(octylphenyl) phosphite, di(2-ethylhexyl) (isooctylphenyl) phosphite, tri(2-cyclohexylphenyl) phosphite), tri-α-naphthyl phosphite, tri(phenylphenyl) phosphite, tri(2-phenylethyl) phosphite, ethylene phenyl phosphite, ethylene t-butyl phosphite, ethylene isohexyl phosphite, ethylene isooctyl phosphite, ethylene cyclohexyl. phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro (5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy) ethyloxy group has an average molecular weight of 350),3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites are: bis(4,4'-thio-bis(2-tertiary-butyl-5-methyl-phenol)) isooctyl phosphite, mono(4,4'-thio-bis(2-tertiary-butyl-5-methyl-phenol)) di-phenyl phosphite, tri-(4,4'-n-butylidene-bis(2-tertiary-butyl-5-methyl-phenol)) phosphite, (4,4'-benzylidene-bis(2-tertiary-butyl-5-methyl-phenol)) di-phenyl phosphite, isooctyl 2,2'-bis(-parahydroxyphenyl) propane phosphite, decyl 4,4'-n-butylidene-bis(2-tertiary-butyl-5-methylphenol) phosphite, tri-4,4'-thio-bis(2-tertiary-butyl-5-methylphenol) phosphite, 2-ethylhexyl-2,2'-methylene-bis(4-methyl-6,1'-methylcyclohexyl) phenol phosphite, tri(2,2'-bis-(para-hydroxyphenyl) propane) phosphite, tri(4,4'-thio-bis(2-tertiary-butyl-5-methyl-phenol) phosphite, isooctyl(2,6-bis(2'-hydroxy-3,5-dinonylbenzyl)-4-nonyl phenyl)) phosphite, tetra-tridecyl-4,4'-n-butylidene-bis(2-tertiary-butyl-5-methylphenyl) diphosphite, tetra-isooctyl-4,4'-thio-bis(2-tertiary-butyl-5-methylphenyl) diphosphite, 2,2'-methylene-bis(4-methyl-6,1'-methyl cyclohexyl phenyl) polyphosphite, isooctyl-4,4'-isopropylidene-bis-phenyl polyphosphite, 2-ethylhexyl-2,2'-methylene-bis(4-methyl-6,1'-methyl-cyclohexyl) phenyl triphosphite, tetra-tridecyl-4,4'-oxydiphenyl diphosphite, tetra-n-dodecyl-4,4'-n-butylidene bis(2-tertiarybutyl-5-methylphenyl) diphosphite, tetra-tridecyl-4,4'-isopropylidene bisphenyl diphosphite, hexa-tridecyl butane-1,1,3-tris(2'-methyl-5'-tertiary-butylphenyl-4') triphosphite.

Exemplary acid phosphites are di(phenyl) phosphite, monophenyl phosphite, mono(diphenyl) phosphite, dicresyl phosphite, di-(o-isooctylphenyl) phosphite, di(p-ethylhexylphenyl) phosphite, di(p-t-octylphenyl) phosphite, di(dimethylphenyl) phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl) phosphite, monocyclohexyl phosphite, dicyclohexyl phosphite, di(2-cyclohexyl phenyl) phosphite, di-α-naphthyl phosphite, diphenyl phenyl phosphite, di(diphenyl) phosphite, di-(2-phenyl ethyl) phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol)) phosphite, (4,4'-thio-bis(2-tertiary-butyl-5-methylphenol)) phenyl phosphite, bis(4,4'-n-butylidene-bis(2-tertiary-butyl-5-methylphenol)) phosphite, mono(4,4'-benzylidene-bis(2-tertiary-butyl-5-methylphenol)) phosphite, mono(2,2'-bis-(parahydroxyphenyl)propane) phosphite, mono(4,4'-butylidene-bis(2-tertiary-butyl-5-methylphenol) phosphite, bis(4,4'-thio-bis(2-tertiary-butyl-5-methylphenol)) phosphite, mono-2-ethylhexyl-mono-2,2'-methylene-bis(4-methyl-6,1'-methylcyclohexyl) phenol phosphite, bis(2,2'-bis(para-hydroxyphenyl)propane) phosphite, monoisooctylmono(4,4'-thio-bis(2-tertiary-butyl-5-methylphenol)) phosphite, isooctyl-(2,6-bis(2'-hydroxy-3,5-dinonylbenzyl)-4-nonylphenyl)) phosphite, tri-tridecyl-4,4'-n-butylidene-bis(2-tertiary-butyl-5-methylphenyl) diphosphite, triisooctyl-4,4'-thio-bis(2-tertiary-butyl-5-methylphenyl) diphosphite, bis(2,2'-methylene-bis(4-methyl-6,1'-methyl cyclohexyl phenyl)) phosphite, isooctyl-4,4'-isopropylidene-bis-phenyl phosphite, monophenyl mono(2,2'-methylene-bis(4-methyl-6,1'-methyl-cyclohexyl)) triphosphite, di-tridecyl-4,4'-oxydiphenyl diphosphite, di-n-dodecyl- 4,4'-n-butylidene-bis(2-tertiary-butyl-5-methylphenyl) diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

$$R_1OOCCH_2CH_2—S—CH_2CH_2COOY$$

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$$—XO[OCCH_2CH_2SCH_2CH_2COOXO]_nOCCH_2CH_2—S—CH_2CH_2COOZ$$

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylenearylene and mixed alkylenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:

| | |
|---|---|
| $R_1OOCCH_2CH_2SCH_2CH_2COOH$ | (a) |
| $R_1OOCCH_2CH_2SCH_2CH_2COOR_2$ | (b) |
| $R_1O[OCCH_2CH_2SCH_2CH_2COOX—O]_n OCCH_2CH_2SCH_2CH_2COOZ$ | (c) |
| $R_1OOCCH_2CH_2SCH_2CH_2COOM$ | (d) |

In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

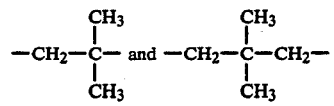

arylene radicals such as phenylene

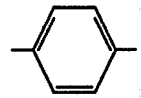

methylenephenylene

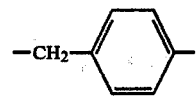

dimethylene phenylene

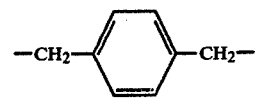

and alicyclylene such as cyclohexylene

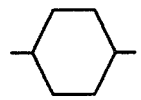

and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl) thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

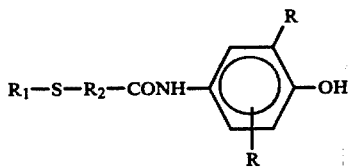

R is alkyl of one to either carbon atoms, $R_1$ is alkyl of six to twenty-four carbon atoms, and $R_2$ is alkylene of one to six carbon atoms.

(2) Thioalkanoic acid amides of 1,3,5-triazines of Ozeki et al Japanese Pat. No. 20,366/68 having the formula:

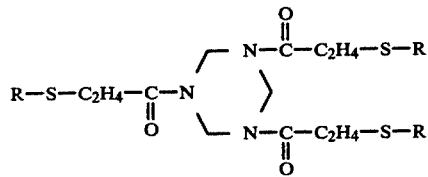

R is alkyl of eight to eighteen carbon atoms.

(3) Bis-thioalkanoic acid amides of Yamamoto et al Japanese Pat. No. 23,765/68 having the formula:

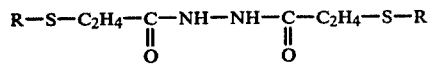

R is alkyl of more than six carbon atoms, aryl or aralkyl.

(4) Bis-thioalkylanoic acid amides of Ozeki et al Japanese Pat. No. 26,184/69 having the formula:

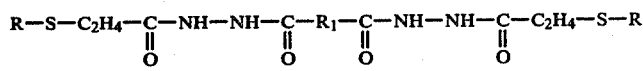

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

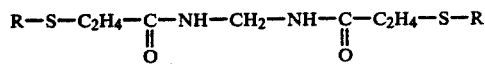

R is alkyl or more than six carbon atoms, aryl, or aralkyl.

(6) Thioalkanoic acid amide derivatives of Minagawa et al, published Japanese application No. 106,484/74 having the formula:

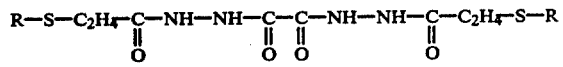

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

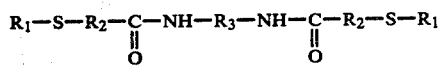

wherein:
$R_1$ is alkyl having from one to about fifty carbon atoms;
$R_2$ is alkylene having from one to about three carbon atoms; and
$R_3$ is alkylene having from about two to about twelve carbon atoms.

β-Alkylthiopropionic acid esters having the general formula:

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl) benzotriazoles, 2(2-hydroxy-3-t-butyl-5-methylphenyl)-5-chlorobenzotriazole, 2(2-hydroxy-3-5-di-t-butylphenyl)-5-chlorobenzotriazole, 2(2-hydroxy-3,5-di-t-amylphenyl) benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octyl-phenolate), nickel-monoethyl(3,5-di-t-butyl-4-hydroxybenzyl) phosphonate, substituted acrylonitriles such as methyl-α-cyano-β-methyl-β-(p-methoxy phenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 10% total stabilizers including the tetrapiperidinyl ester by weight of the polymer are satisfactory. Preferably, from 0.01 to 5% is employed for optimum stabilization.

The stabilizer systems of the invention are readily rendered in solid particulate form, comprising a blend of:

(a) tetrapiperidinyl ester light stabilizer in an amount of from about 10 to about 35 parts by weight; and optionally:

(b) a phenolic antioxidant in an amount from about 10 to about 35 parts by weight; and/or (c) other heat or light stabilizers in an amount of from about 10 to about 35 parts by weight.

The tetrapiperidinyl esters of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadienestyrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

EXAMPLES 1 TO 8

Polypropylene compositions were prepared using stabilizers of the invention and two of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table I | 0.3 |

The compositions were thoroughly blended in a Brabender Plastograph, and then compression-molded to form sheets 0.3 mm thick. Pieces 2.5 cm$^2$ were cut off from the sheets and exposed to a high voltage mercury lamp with and without immersion in hot water at 80° C. for 15 hours. The hours to failure were noted, and are shown in Table I.

TABLE I

| | | Hours to Failure | |
|---|---|---|---|
| Example No. | Stabilizer | Without Immersion | After Immersion for 15 hours |
| Control 1 | Tetra(2,2,6,6-tetramethyl-4-piperidyl) pyromellitate | 460 | 330 |
| Control 2 | Tetra(2,2,6,6-tetramethyl-4-piperidyl)-7-bicyclo[2,2,2]octane-2,3,5,6-tetra carboxylate | 530 | 410 |

TABLE I-continued
| Example No. | Stabilizer | Hours to Failure Without Immersion | After Immersion for 15 hours |
|---|---|---|---|
| Example 1 | 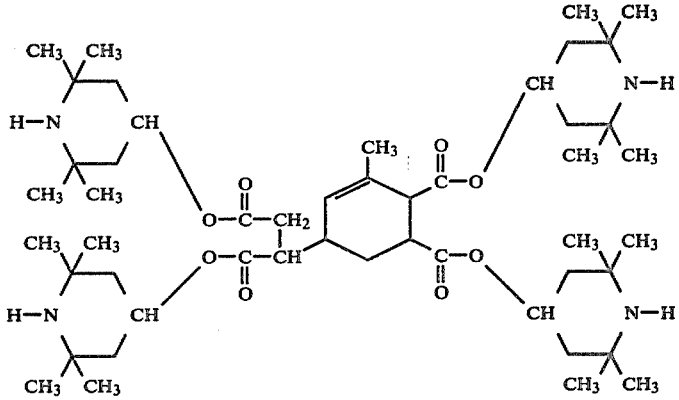 | 730 | 650 |
| Example 2 | 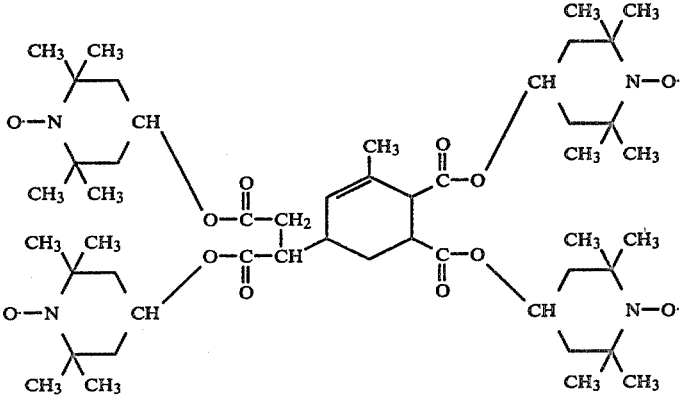 | 710 | 620 |
| Example 3 | 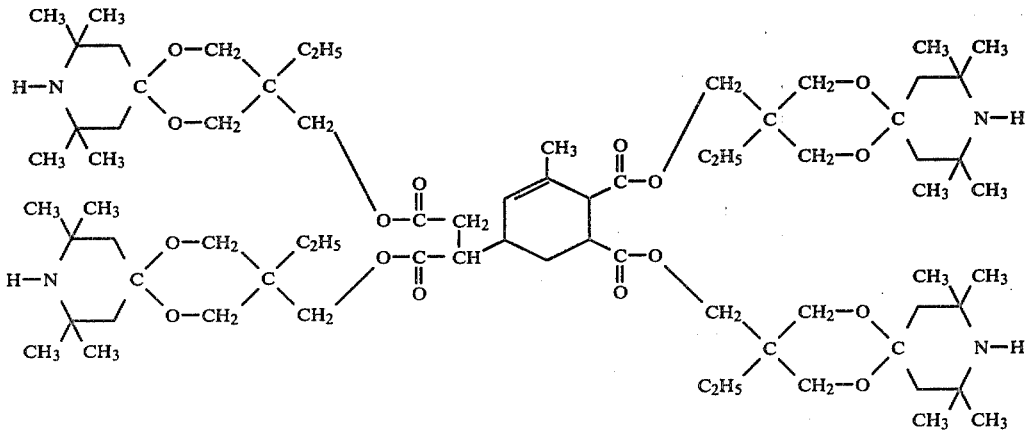 | 690 | 630 |
| Example 4 | | 690 | 620 |

TABLE I-continued
| Example No. | Stabilizer | Hours to Failure Without Immersion | Hours to Failure After Immersion for 15 hours |
|---|---|---|---|
| | 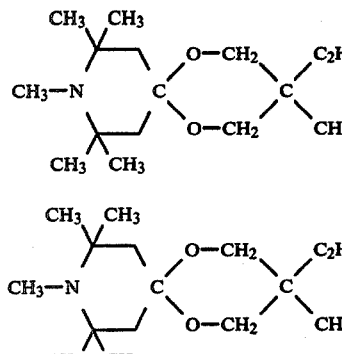 | | |
| Example 5 | 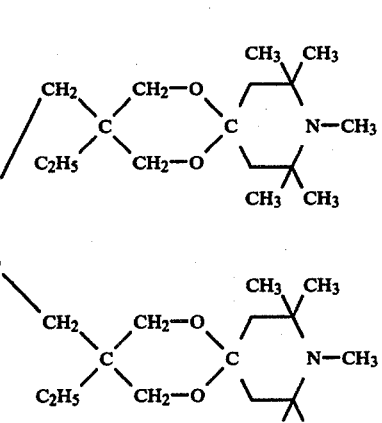 | 660 | 600 |
| Example 6 | 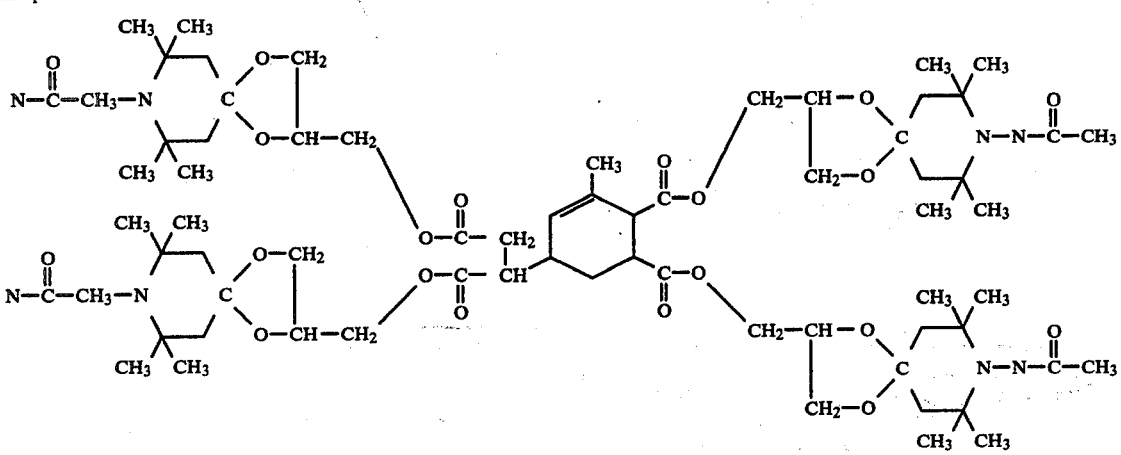 | 710 | 640 |
| Example 7 | | 680 | 610 |

TABLE I-continued

| Example No. | Stabilizer | Hours to Failure Without Immersion | Hours to Failure After Immersion for 15 hours |
|---|---|---|---|
| | 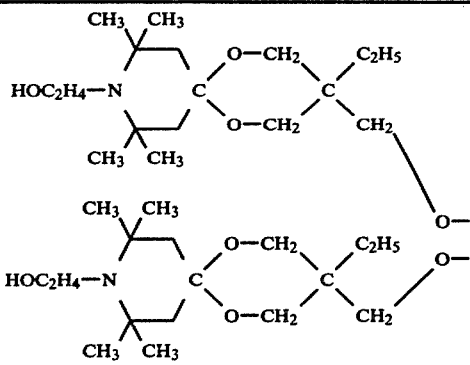 | | |
| Example 8 | 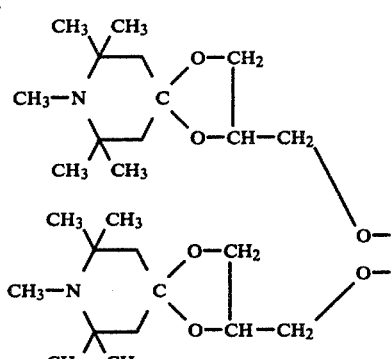 | 650 | 600 |

The tetrapiperidinyl carboxylic acid esters of the invention are clearly superior to the controls.

EXAMPLES 9 TO 16

Conventional stabilizers for polymeric materials may lose their effectiveness because of volatilization or decomposition at high polymer processing temperatures. This is not true of the stabilizers of the invention, as shown by observing the effect of heat in repeated extrusions of ethylenepropylene copolymer compositions. These compositions were prepared using stabilizers of the invention and of the prior art, and having the following formulation:

| Ingredient | Parts by Weight |
|---|---|
| Ethylene-propylene copolymer | 100 |
| Ca stearate | 0.2 |
| Stearyl-(3,5-di-t-butyl-4-hydroxyphenyl) propionate | 0.1 |
| Dilauryl thiodipropionate | 0.2 |
| Stabilizer as shown in Table II | 0.2 |

The ingredients were mixed and the compositions then extruded (cylinder temperature 230° C. and 240° C., head die temperature 250° C., velocity 20 rpm) five times. Test pieces were then molded by injection molding at 250° C. The test pieces were exposed to a high voltage mercury lamp; the hours to failure were noted, and are shown in Table II.

TABLE II

| Example No. | Stabilizer | Hours to Failure Extruded 1 time | Hours to Failure Extruded 5 times |
|---|---|---|---|
| Control 1 | Tetra(2,2,6,6-tetramethyl-4-piperidyl)-1,1,2,3-propanetetracarboxylate | 420 | 280 |
| Control 2 | Tetra(2,2,6,6-tetramethyl-4-piperidyl)-7-bicylco[2,2,2]octene-2,3,5,6-tetracarboxylate | 380 | 290 |

TABLE II-continued

| Example No. | Stabilizer | Hours to Failure Extruded 1 time | Hours to Failure Extruded 5 times |
|---|---|---|---|
| Example 9 | (structure) | 550 | 490 |
| Example 10 | (structure) | 540 | 480 |
| Example 11 | | 520 | 480 |
| Example 12 | (structure) | 490 | 440 |

TABLE II-continued
| | | Hours to Failure | |
|---|---|---|---|
| | | Extruded | Extruded |
| Example No. | Stabilizer | 1 time | 5 times |
| | 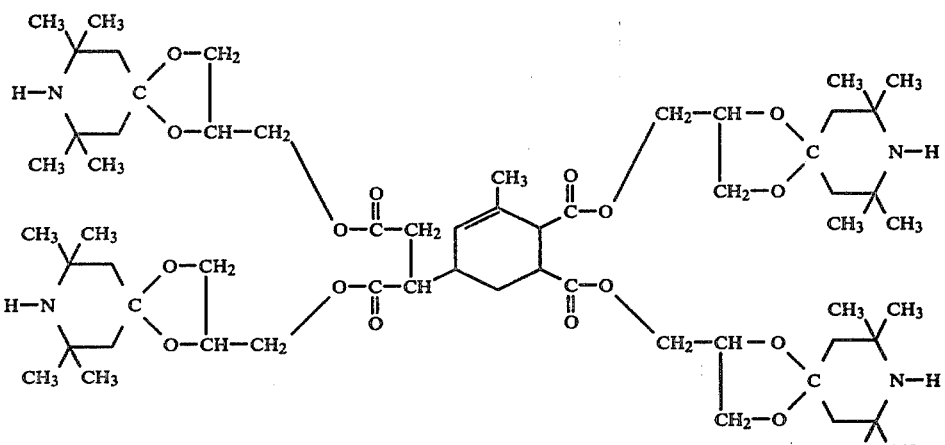 | | |
| Example 13 | 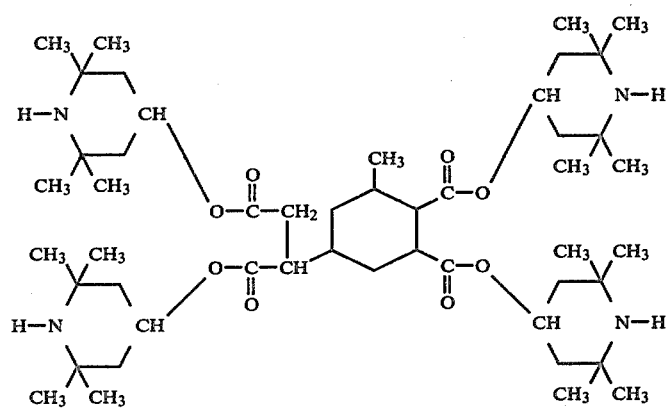 | 530 | 470 |
| Example 14 | 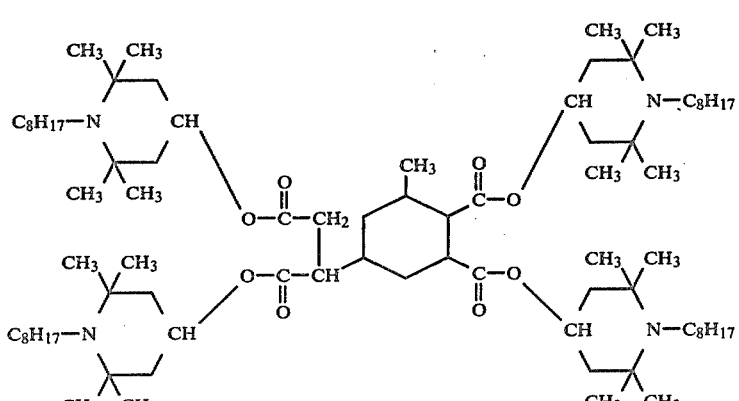 | 490 | 430 |
| Example 15 | | 480 | 440 |

TABLE II-continued

| Example No. | Stabilizer | Hours to Failure Extruded 1 time | Extruded 5 times |
|---|---|---|---|
| Example 16 | | 480 | 430 |

The tetrapiperidinyl carboxylic acid esters of the invention are clearly superior to the controls.

EXAMPLES 17 TO 24

High density polyethylene compositions were prepared using the stabilizers of the invention and three of the prior art, and having the following formulation:

| Ingredient | Parts by Weight |
|---|---|
| High-density polyethylene | 100 |
| Ca stearate | 1 |
| Tetrakis-(methylene-3-(3,5-di-t-butyl-4-hydroxyphenyl) propionate)methane | 0.1 |
| Distearylthiodipropionate | 0.3 |
| Stabilizer as shown in Table III | 0.2 |

The stabilizer was blended with the polymer on a two-roll mill and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and is reported in Table III.

TABLE III

| Example No. | Stabilizer | Hours to Failure |
|---|---|---|
| Control 1 | Tetra(2,2,6,6-tetramethyl-4-piperidyl)pyromellitate | 680 |
| Con- | Tetra(2,2,6,6-tetramethyl-4-piperidyl)-7-bicyclo[2,2,2]octene-2,3,5,6-tetracarboxylate | 850 |

TABLE III-continued

| Example No. | Stabilizer | Hours to Failure |
|---|---|---|
| trol 2 | | |
| Example 17 | [chemical structure] | 1,130 |
| Example 18 | [chemical structure] | 1,100 |
| Example 19 | [chemical structure] | 1,070 |

TABLE III-continued

| Example No. | Stabilizer | Hours to Failure |
|---|---|---|
| Example 20 | [structure] | 1,070 |
| Example 21 | [structure] | 1,020 |
| Example 22 | [structure] | 1,110 |

TABLE III-continued

| Example No. | Stabilizer | Hours to Failure |
|---|---|---|
| Example 23 | (structure shown) | 1,050 |
| Example 24 | (structure shown) | 1,030 |

The tetrapiperidinyl carboxylic acid esters of the invention are clearly superior to the controls.

EXAMPLES 25 TO 32

Ethylene-vinyl acetate copolymers compositions were prepared using stabilizers of the invention and three of the prior art, and having the following formulation:

| Ingredient | Parts by Weight |
|---|---|
| Ethylene-vinylacetate copolymer | 100 |
| 2,6-Di-t-butyl-p-cresol | 0.1 |
| Ca stearate | 0.1 |
| Zn stearate | 0.1 |
| Diisodecylphenylphosphite | 0.2 |
| Stabilizer as shown in Table IV | 0.2 |

The stabilizer was blended with the polymer on a two-roll roll mill at 130° C., and sheets 0.4 mm thick were then compression-molded at 140° C. from the resulting blend. Pieces 2.5 cm square were cut off from the sheets and exposed to ultraviolet light in a Weather-O-Meter for 500 hours. At the start and at the conclusion of the test, tensile strength of the sheet samples was determined. The results are shown in Table IV as % retention of the initially determined tensile strength.

TABLE IV

| Example No. | Stabilizer | % Retention of Tensile Strength after 500 hours |
|---|---|---|
| Control 1 | Tetra(2,2,6,6-tetramethyl-4-piperidyl)pyromellitate | 62 |
| Control 2 | Tetra(2,2,6,6-tetramethyl-4-piperidyl)-7-bicyclo[2,2,2]octene-2,3,5,6-tetracarboxylate | 69 |

TABLE IV-continued

| Example No. | Stabilizer | % Retention of Tensile Strength after 500 hours |
|---|---|---|
| Example 25 | (structure) | 81 |
| Example 26 | (structure) | 81 |
| Example 27 | (structure) | 78 |
| Example 28 | | 77 |

TABLE IV-continued

| Example No. | Stabilizer | % Retention of Tensile Strength after 500 hours |
|---|---|---|
| Example 29 | [chemical structure] | 75 |
| Example 30 | [chemical structure] | 80 |
| Example 31 | | 77 |

TABLE IV-continued

| Example No. | Stabilizer | % Retention of Tensile Strength after 500 hours |
|---|---|---|
| Example 32 | (structure shown) | 76 |

The tetrapiperidinyl carboxylic acid esters of the invention are clearly superior to the controls.

EXAMPLES 33 TO 40

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2 |
| Tris nonyl phenyl phosphite | 0.2 |
| Ca stearate | 1.0 |
| Zn stearate | 0.1 |
| Stabilizer as shown in Table V | 0.3 |

This formulation was blended and sheeted off on a two-roll mill to form sheets 1 mm thick. The light resistance of these sheets was then determined by placing strips 1 cm wide in a Weather-O-Meter; and exposing them to ultraviolet light. The time in hours was then noted for the sheets to develop a noticeable discoloration and/or embrittlement, indicating deterioration due to oxidation in the presence of ultraviolet light. The following results were obtained.

TABLE V

| Example No. | Stabilizer | Hours to Failure |
|---|---|---|
| Control 1 | None | 200 |
| Control 2 | Tetra(2,2,6,6-tetramethyl-4-piperidyl)pyromellitate | 320 |
| Control 3 | Tetra(2,2,6,6-tetramethyl-4-piperidyl)-7-bicyclo[2,2,2]octene-2,3,5,6-tetracarboxylate | 470 |

TABLE V-continued
| Example No. | Stabilizer | Hours to Failure |
|---|---|---|
| Example 33 | 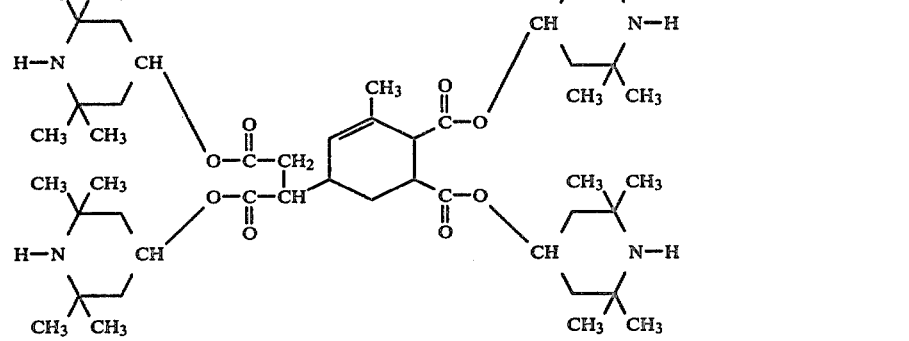 | 660 |
| Example 34 | 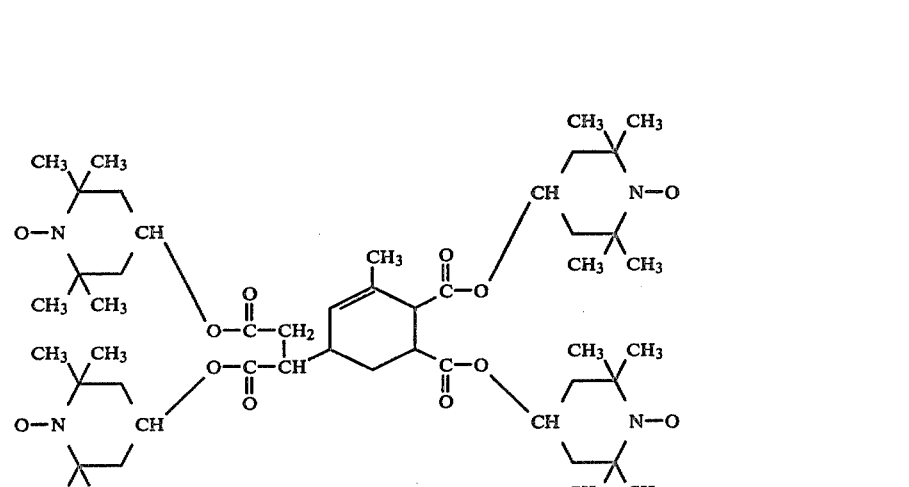 | 730 |
| Example 35 | 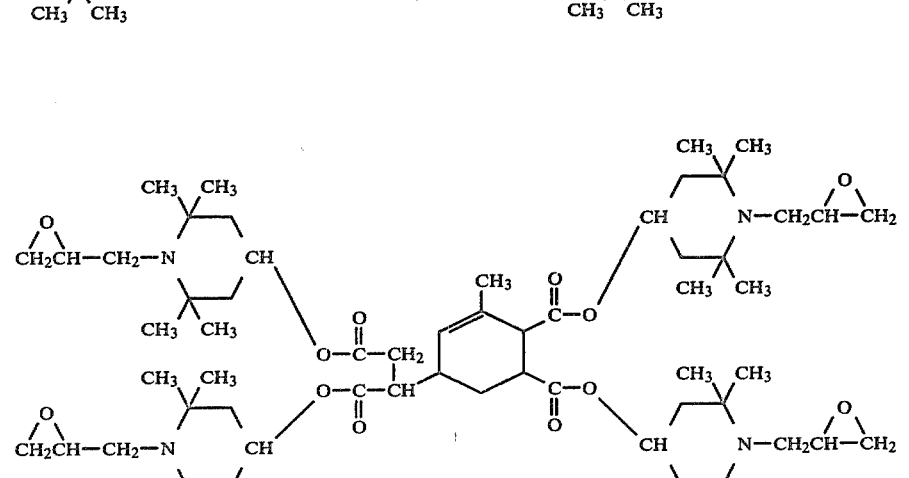 | 720 |
| Example 36 | | 640 |

TABLE V-continued

| Example No. | Stabilizer | Hours to Failure |
|---|---|---|
| Example 37 | [chemical structure] | 660 |
| Example 38 | [chemical structure] | 650 |
| Example 39 | | 700 |

TABLE V-continued

| Example No. | Stabilizer | Hours to Failure |
|---|---|---|

[Structural formula for Example 39 stabilizer: a bis-piperidinyl N-oxide tetraester based on a cyclohexane tetracarboxylate core]

Example 40 — 680

[Structural formula for Example 40 stabilizer: a tetrakis(N-hydroxyethyl piperidinyl) tetraester based on a cyclohexane tetracarboxylate core]

The tetrapiperidinyl carboxylic acid esters of the invention are clearly superior to the controls.

EXAMPLES 41 TO 48

Acrylonitrile-butadiene-styrene terpolymer resin compositions were prepared using stabilizers of the invention and three of the prior art, and having the following formulations:

| Ingredient | Parts by Weight |
|---|---|
| Acrylonitrile-butadiene-styrene terpolymer | 100 |
| 4,4′-butylidene-bis(2-tert-butyl-m-cresol) | 0.1 |
| Stabilizer as shown in Table VI | 0.3 |

The stabilizer was blended with the resin on a two-roll mill, and sheets 3 mm thick were prepared by compression-molding of the resulting blend. Pieces 2.5 cm square were cut off from the sheets, and subjected to ultraviolet light in a Weather-O-Meter for 1000 hours. Tensile strength before and after the test exposure was determined, and the results reported as the percent of tensile strength retained, at the end of this time, in Table VI.

TABLE VI

| Example No. | Stabilizer | % Tensile Strength Retained |
|---|---|---|
| Control 1 | Tetra(2,2,6,6-tetramethyl-4-piperidyl)pyromellitate | 53 |
| Control 2 | Tetra(2,2,6,6-tetramethyl-4-piperiyl)-7-bicyclo[2,2,2]octene-2,3,5,6-tetracarboxylate | 68 |

TABLE VI-continued
| Example No. | Stabilizer | % Tensile Strength Retained |
|---|---|---|
| Example 41 | 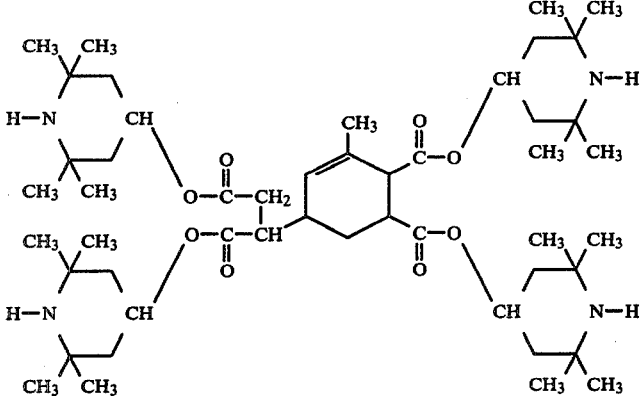 | 79 |
| Example 42 | 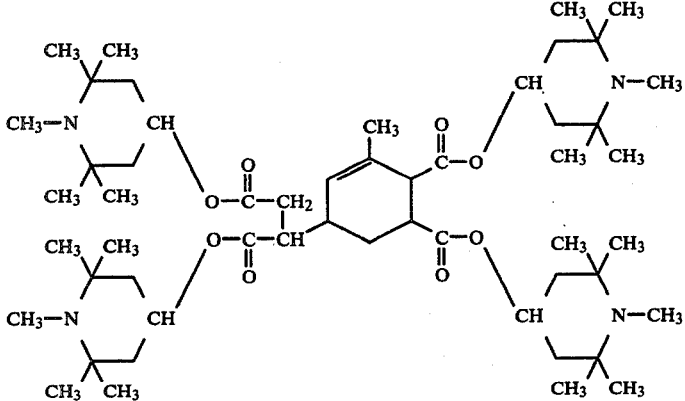 | 79 |
| Example 43 | 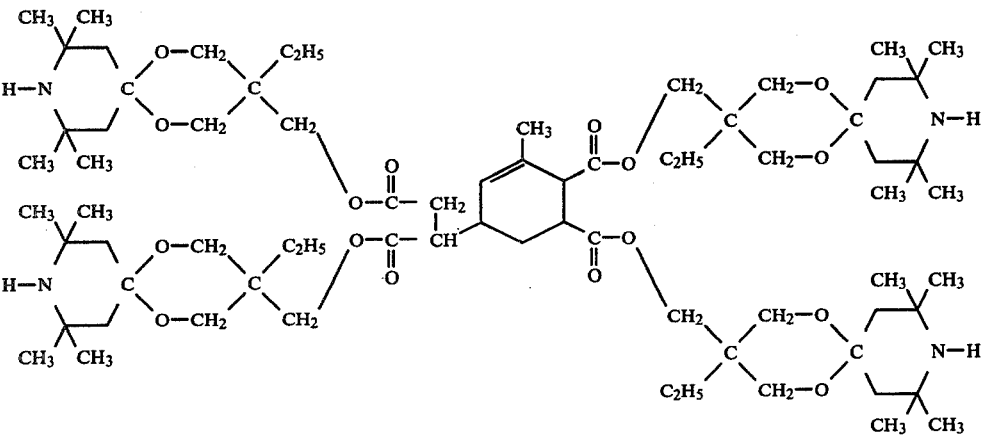 | 76 |

TABLE VI-continued
| Example No. | Stabilizer | % Tensile Strength Retained |
|---|---|---|
| Example 44 | 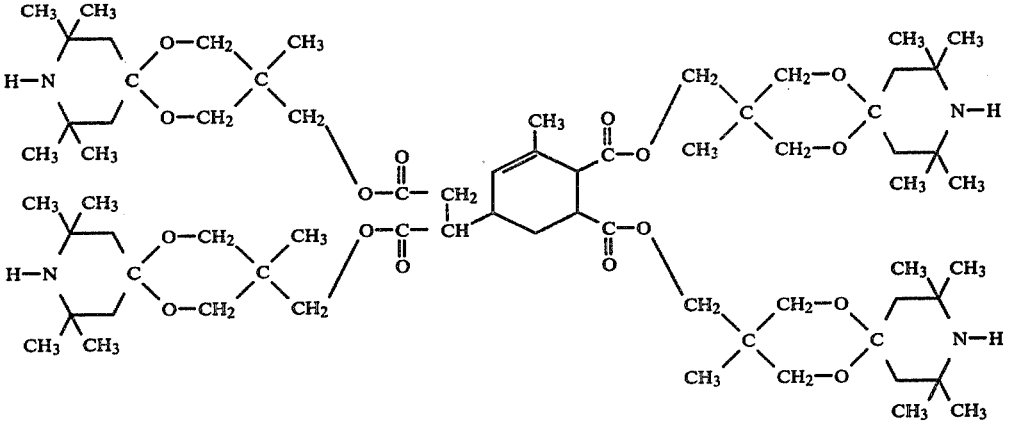 | 76 |
| Example 45 | 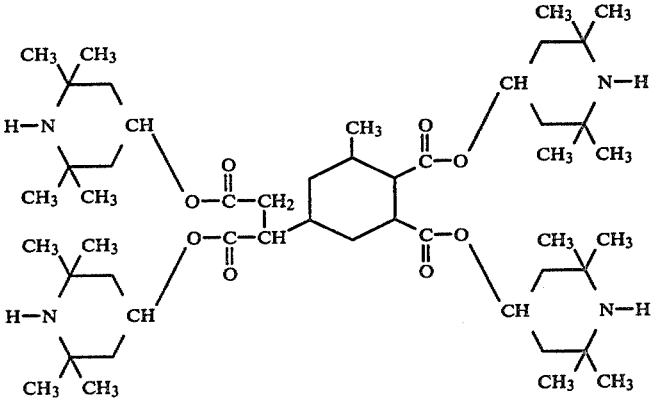 | 78 |
| Example 46 | 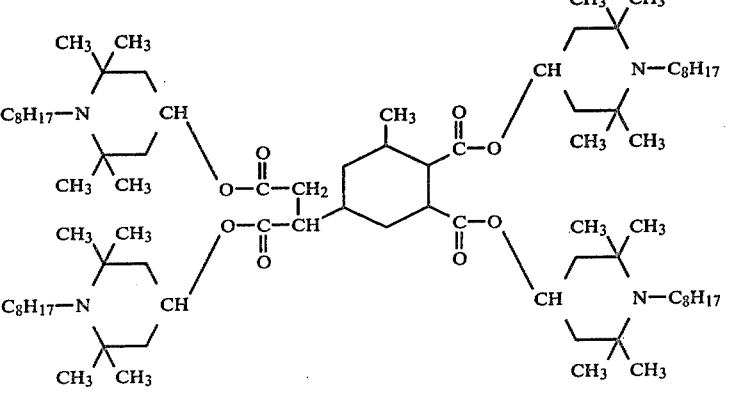 | 75 |

TABLE VI-continued

| Example No. | Stabilizer | % Tensile Strength Retained |
|---|---|---|
| Example 47 | 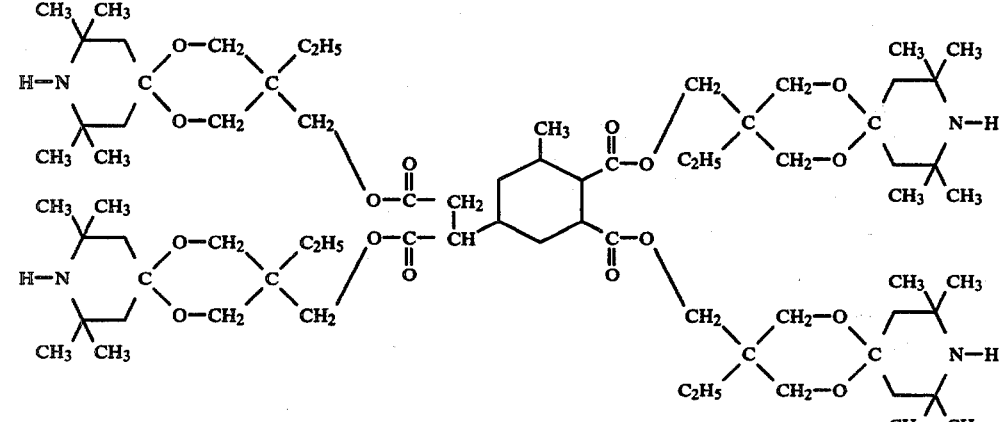 | 75 |
| Example 48 | 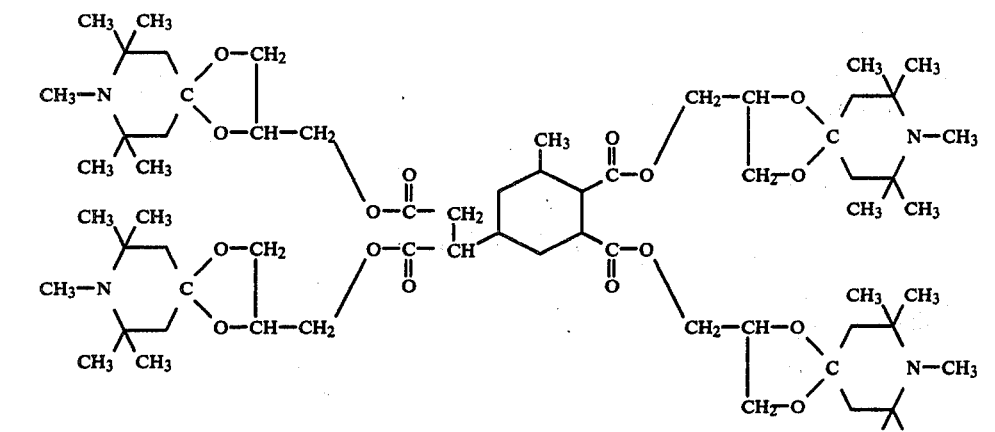 | 74 |

The tetrapiperidinyl carboxylic acid esters of the invention are clearly superior to the controls.

EXAMPLES 49 TO 56

Polyurethane resin compositions were prepared using stabilizers of the invention and having the following formulation:

| Ingredient | Parts by Weight |
|---|---|
| Polyurethane resin (Asahi Denka[1] U-100) | 100 |
| Ba stearate | 0.7 |
| Zn stearate | 0.3 |
| 2,6-di-t-butyl-p-cresol | 0.1 |
| Stabilizer as shown in Table VII | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm square were cut out from the sheets, and exposed to ultraviolet light in a Weather-O-Meter for thirty hours. Elongation before and after exposure was determined, and the percent elongation retained after the exposure is given in Table VII.

TABLE VII

| Example No. | Stabilizer | % Elongation Retained |
|---|---|---|
| Control 1 | Tetra(2,2,6,6-tetramethyl-4-piperidyl)pyromellitate | 53 |
| Control 2 | Tetra(2,2,6,6-tetramethyl-4-piperidyl)-7-bicyclo[2,2,2]octene-2,3,5,6-tetracarboxylate | 61 |

TABLE VII-continued

| Example No. | Stabilizer | % Elongation Retained |
|---|---|---|
| Example 49 | (structure) | 78 |
| Example 50 | (structure) | 77 |
| Example 51 | (structure) | 74 |
| Example 52 | | 72 |

TABLE VII-continued
| Example No. | Stabilizer | % Elongation Retained |
|---|---|---|
| | 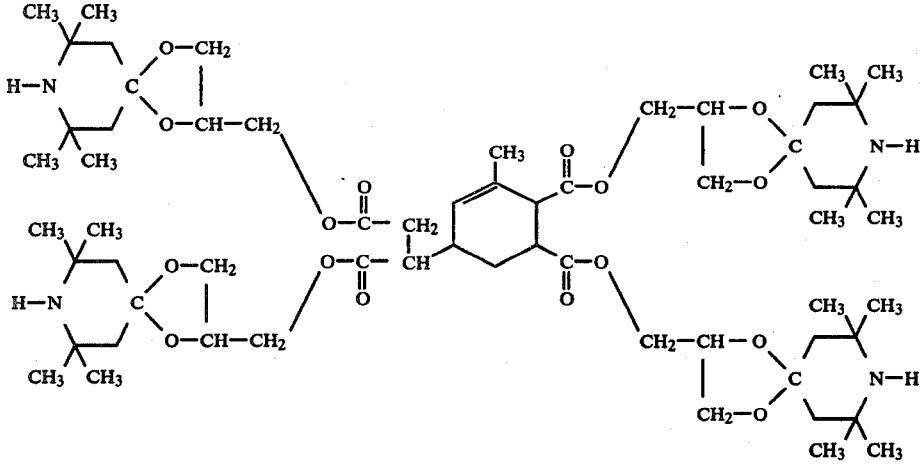 | |
| Example 53 | 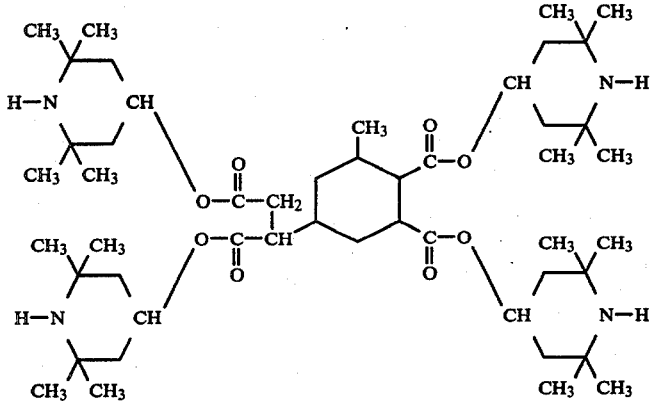 | 78 |
| Example 54 | 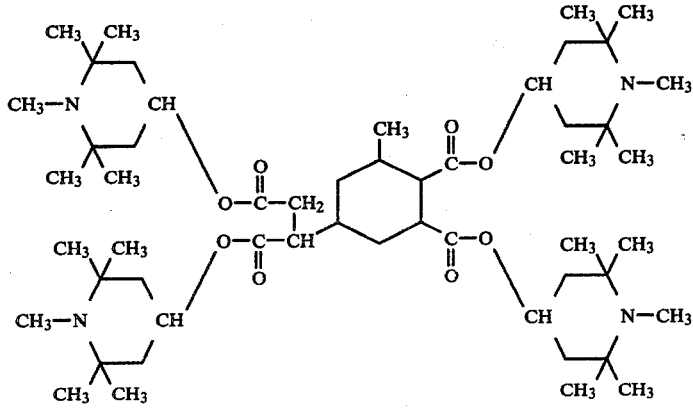 | 77 |
| Example 55 | | 73 |

TABLE VII-continued

| Example No. | Stabilizer | % Elongation Retained |
|---|---|---|
| | 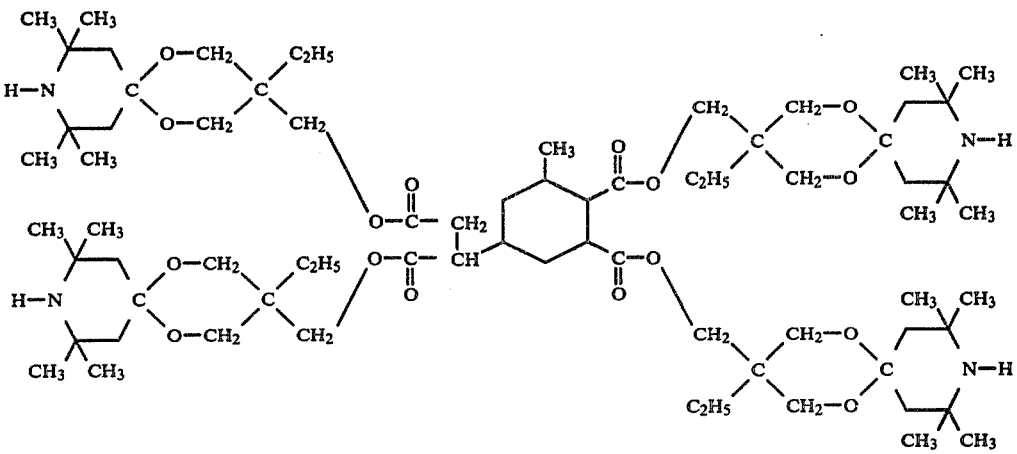 | |
| Example 56 | 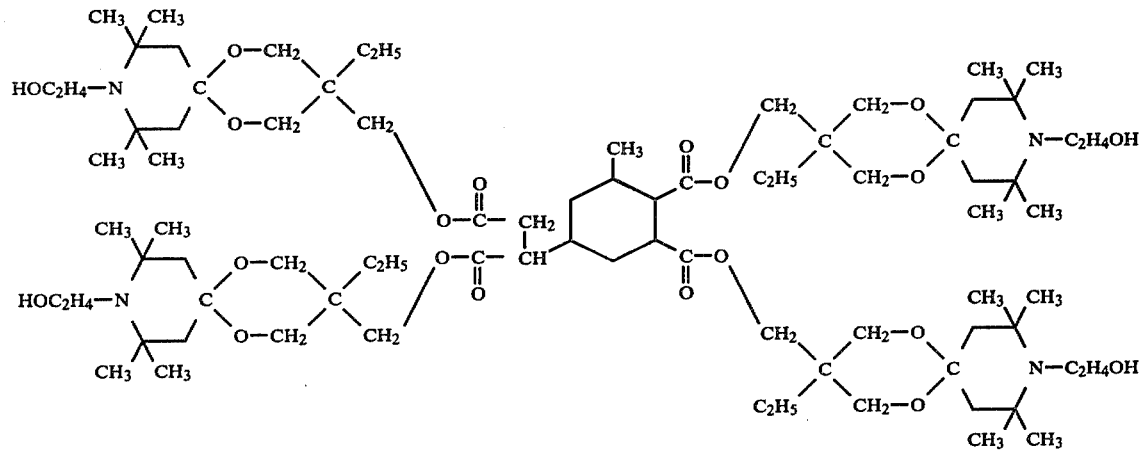 | 72 |

The tetrapiperidinyl carboxylic acid esters of the invention are clearly superior to the controls.

Having regard to the foregoing disclosure, the following is claimed as the inventive and patentable embodiments thereof:

1. Tetra-(2,2,6,6-tetramethyl-4-piperidinyl)-3-methyl-5-(1′,2′-biscarboxylate)-ethyl-cyclohexane or 3-cyclohexene-1,2-dicarboxylates having the formula (I) or (II):

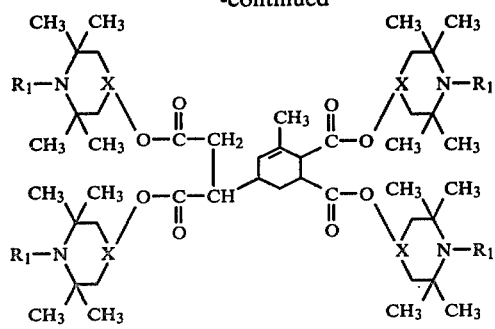

-continued

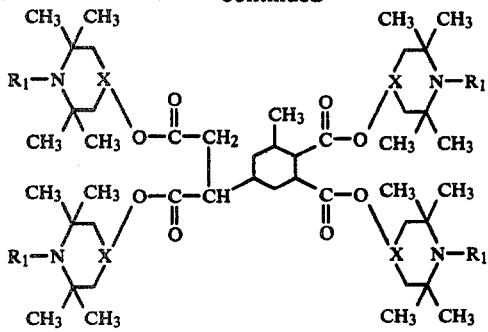

wherein:

R₁ is selected from the group consisting of hydrogen, —O, alkyl, hydroxy alkyl and epoxyalkyl having from one to about eighteen carbon atoms, acyl having from one to about eighteen carbon atoms, cycloalkyl having from three to about eighteen carbon atoms; phenyl; phenalkyl and alkylphenyl having from seven to about twenty-four carbon atoms;

R₂ is lower alkyl having from one to about six carbon atoms; and

X is selected from the group consisting of:

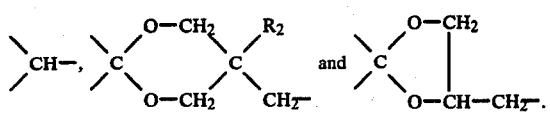

2. Tetramethyl piperidinyl carboxylates according to claim 1 having the formula:

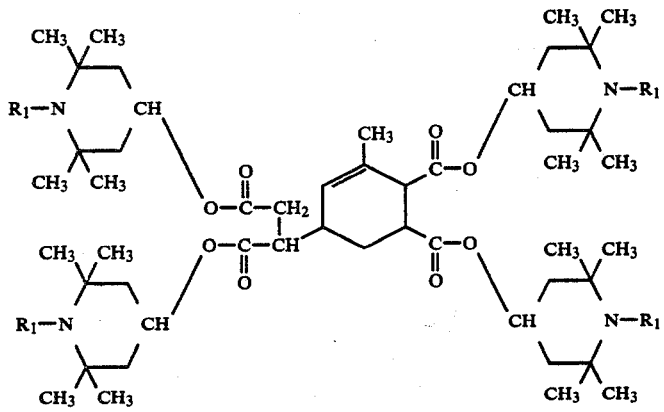

3. Tetramethyl piperidinyl carboxylates according to claim 1 having the formula:

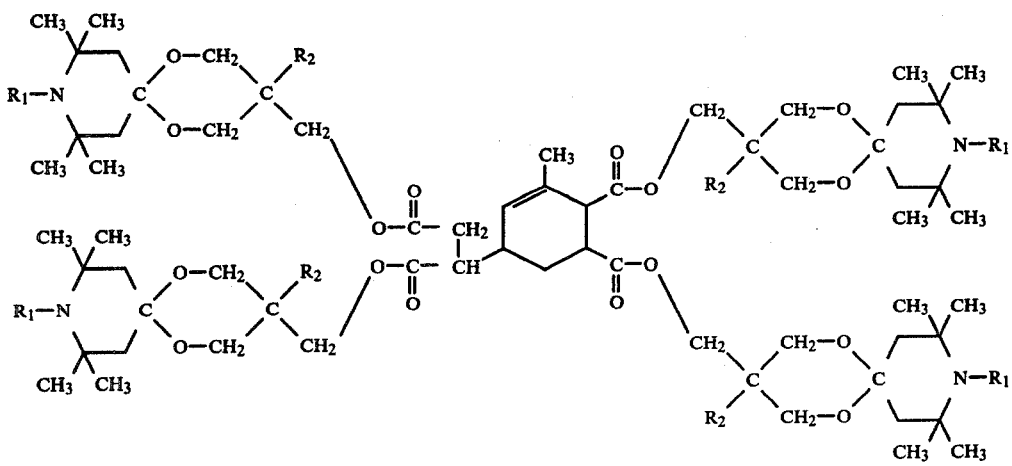

4. Tetramethyl piperidinyl carboxylates according to claim 1 having the formula:

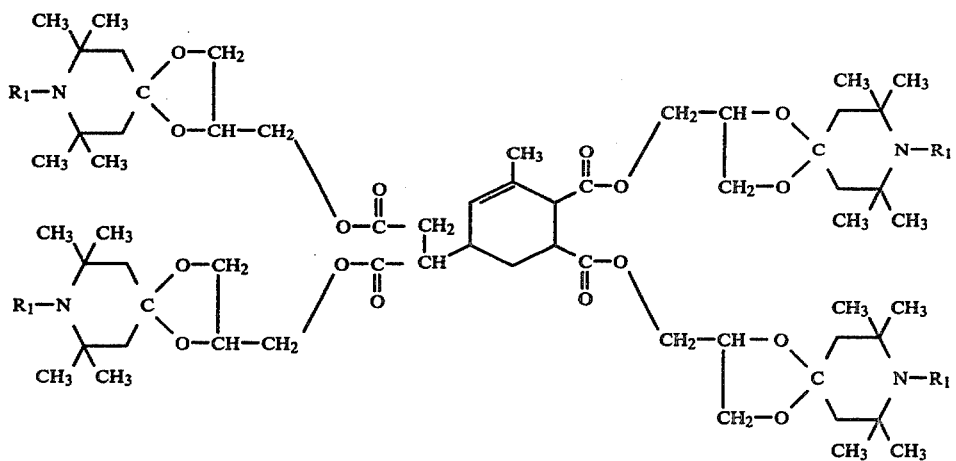
5. Tetramethyl piperidinyl carboxylates according to claim 1 having the formula:
6. Tetramethyl piperidinyl carboxylates according to claim 1 having the formula:
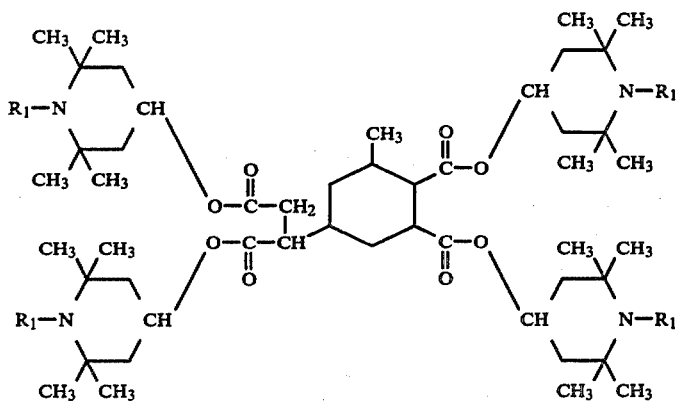
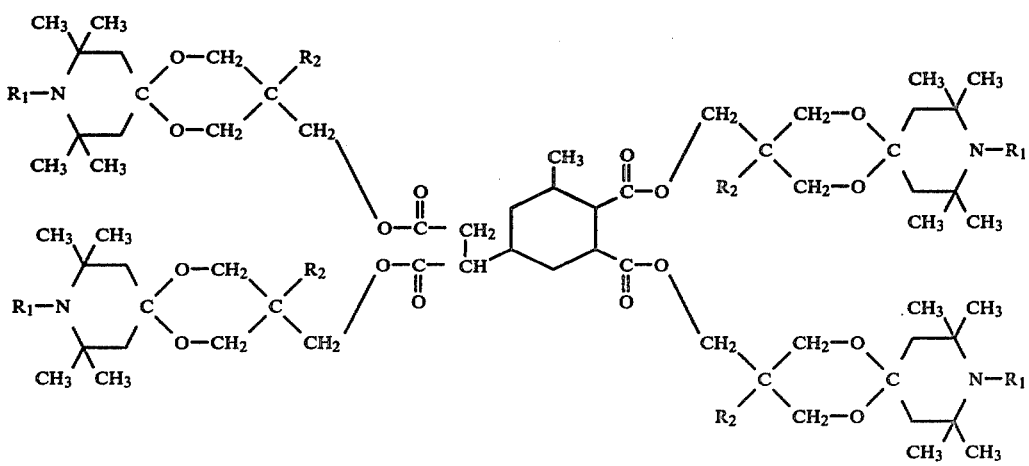
7. Tetramethyl piperidinyl carboxylates according to claim 1 having the formula:

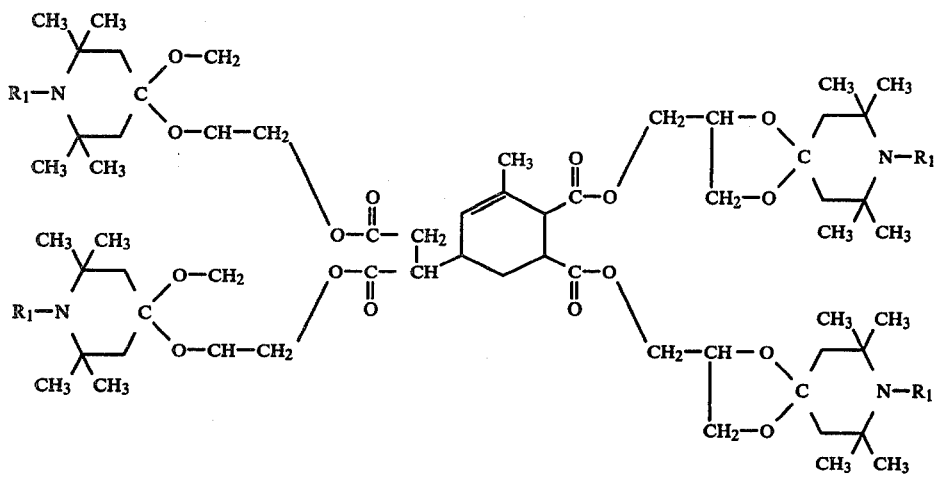

8. Tetramethyl piperidinyl carboxylates according to claim 1 in which $R_1$ is H.

9. Tetramethyl piperidinyl carboxylates according to claim 1 in which $R_1$ is O.

10. Tetramethyl piperidinyl carboxylates according to claim 1 in which $R_1$ is hydroxyalkyl.

11. Tetramethyl piperidinyl carboxylates according to claim 1 in which $R_1$ is epoxyalkyl.

12. Tetramethyl piperidinyl carboxylates according to claim 1 in which $R_1$ is acyl.

13. Tetramethyl piperidinyl carboxylates according to claim 1 in which $R_1$ is cycloalkyl.

14. Tetramethyl piperidinyl carboxylates according to claim 1 in which $R_1$ is phenyl.

15. Tetramethyl piperidinyl carboxylates according to claim 1 in which $R_1$ is phenalkyl.

16. Tetramethyl piperidinyl carboxylates according to claim 1 in which $R_1$ is alkylphenyl.

17. Tetramethyl piperidinyl carboxylates according to claim 1 in which X is >CH.

18. Tetramethyl piperidinyl carboxylates according to claim 1 in which X is

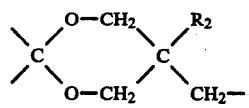

19. Tetramethyl piperidinyl carboxylates according to claim 1 in which X is

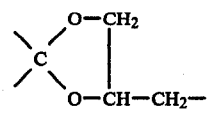

20. Tetramethyl piperidinyl carboxylates according to claim 1 having the structure:

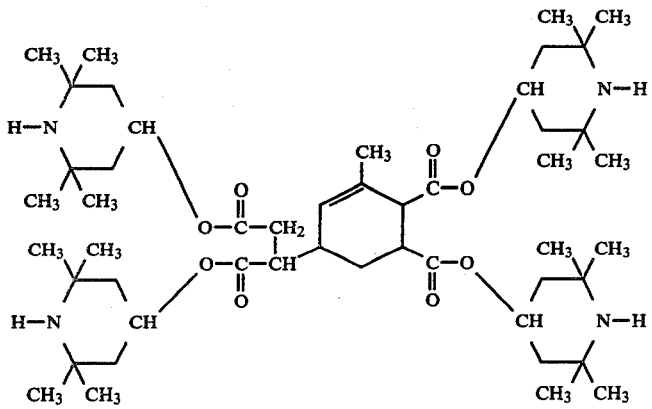

21. Tetramethyl piperidinyl carboxylates according to claim 1 having the structure:

22. Tetramethyl piperidinyl carboxylates according to claim 1 having the structure:
23. Tetramethyl piperidinyl carboxylates according to claim 1 having the structure:
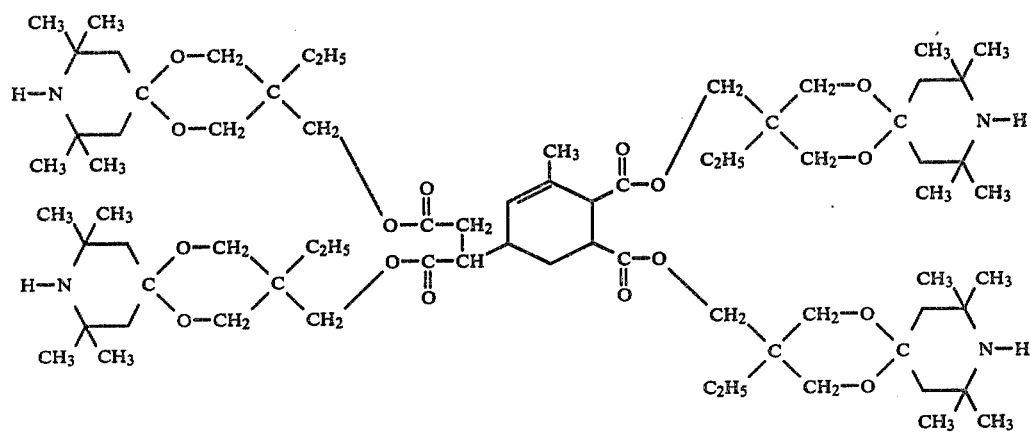
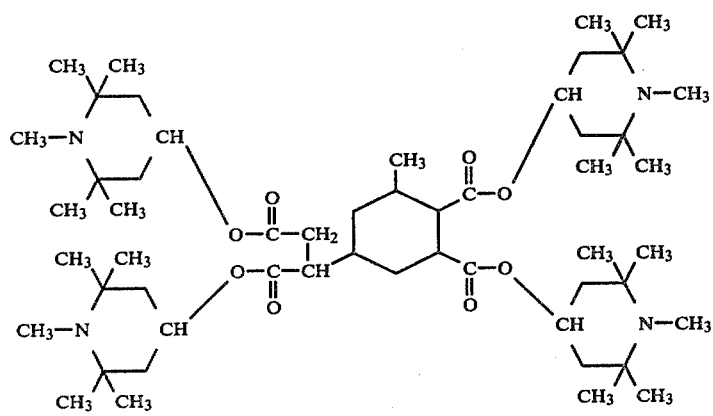
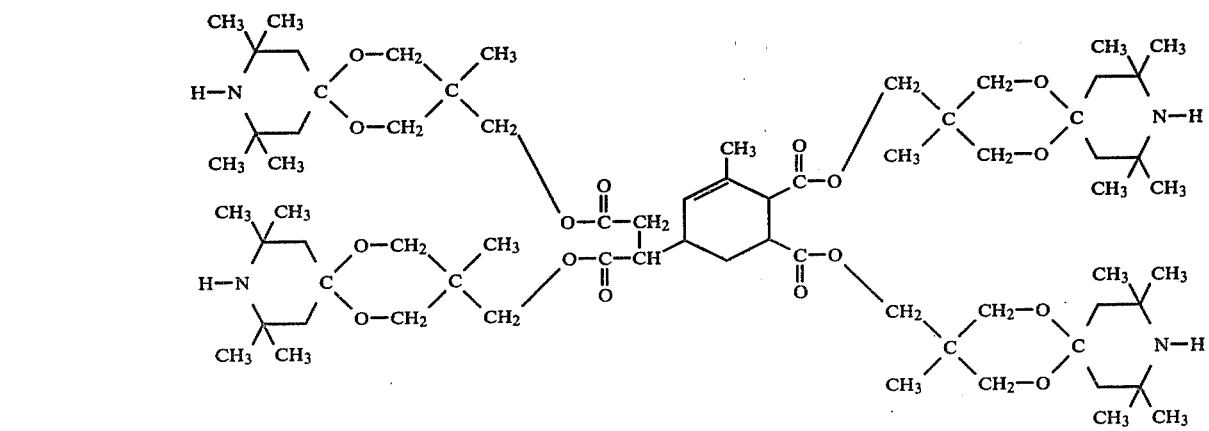
24. Tetramethyl piperidinyl carboxylates according to claim 1 having the structure:

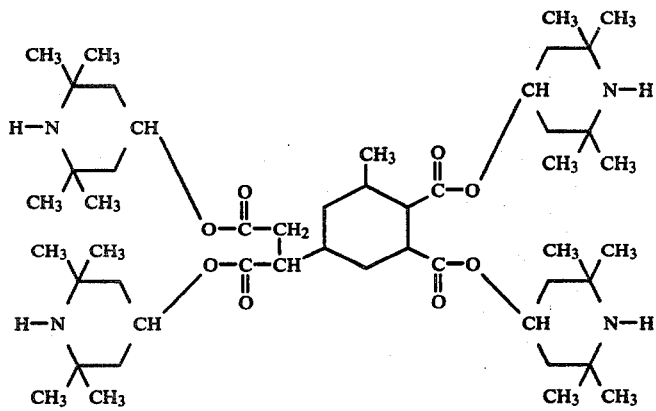

25. Tetramethyl piperidinyl carboxylates according to claim 1 having the structure:

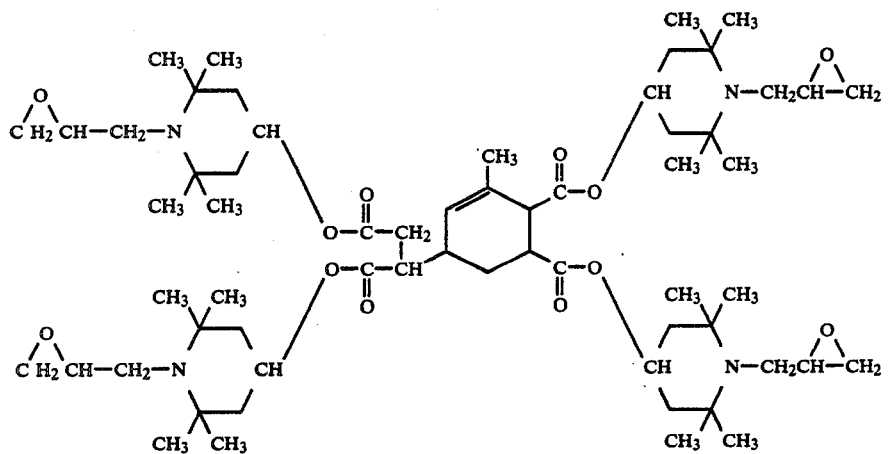

26. Tetramethyl piperidinyl carboxylates according to claim 1 having the structure:

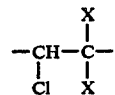

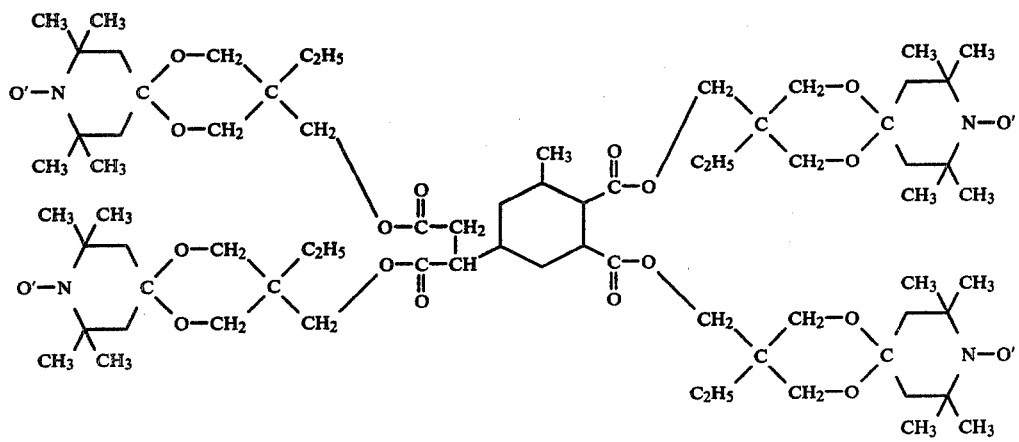

27. A polyvinyl chloride resin composition having improved resistance to deterioration when heated at 350° F., comprising a polyvinyl chloride resin formed at least in part of the recurring group:

and having a chlorine content in excess of 40%, where X is either hydrogen or chlorine; and a compound in accordance with claim 1.

28. A polyvinyl chloride resin composition in accordance with claim 27 in which the polyvinyl chloride resin is polyvinyl chloride homopolymer.

29. A polyvinyl chloride resin composition in accordance with claim 27 in which the polyvinyl chloride resin is a copolmer of vinyl chloride and vinyl acetate.

30. An olefin polymer composition having improved resistance to deterioration comprising an olefin polymer selected from the group consisting of polymers of alpha-olefins having from two to six carbon atoms and polystyrene, and a compound in accordance with claim 1.

31. An olefin polymer composition in accordance with claim 30 wherein the polyolefin is polypropylene.

32. An olefin polymer composition in accordance with claim 30 wherein the polyolefin is polyethylene.

33. An acrylonitrile-butadiene-styrene polymer having its resistance to deterioration when heated at 300° F. and above enhanced by a compound in accordance with claim 1.

34. A polyester resin composition having improved resistance to deterioration comprising a polyester resin and a compound in accordance with claim 1.

35. An ethylene-vinyl acetate copolymer composition having improved resistance to deterioration comprising an ethylene-vinyl acetate copolymer and a compound in accordance with claim 1.

36. A polyurethane composition having improved resistance to deterioration comprising a polyurethane and a compound in accordance with claim 1.

* * * * *